US012188838B2

(12) United States Patent
Petersen

(10) Patent No.: US 12,188,838 B2
(45) Date of Patent: Jan. 7, 2025

(54) COMPACT, DIFFERENTIAL, COAXIAL INDUCTIVE FORCE SENSOR

(71) Applicant: Intuitive Surgical Operations, Inc., Sunnyvale, CA (US)

(72) Inventor: Alan W. Petersen, Cupertino, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 237 days.

(21) Appl. No.: 17/642,892

(22) PCT Filed: Sep. 14, 2020

(86) PCT No.: PCT/US2020/050696
§ 371 (c)(1),
(2) Date: Mar. 14, 2022

(87) PCT Pub. No.: WO2021/055276
PCT Pub. Date: Mar. 25, 2021

(65) Prior Publication Data
US 2023/0003596 A1  Jan. 5, 2023

Related U.S. Application Data

(60) Provisional application No. 62/901,729, filed on Sep. 17, 2019.

(51) Int. Cl.
*G01L 5/164* (2020.01)
*A61B 34/35* (2016.01)
(Continued)

(52) U.S. Cl.
CPC .............. *G01L 5/164* (2013.01); *A61B 34/35* (2016.02); *G01L 1/127* (2013.01); *G01L 5/0038* (2013.01);
(Continued)

(58) Field of Classification Search
CPC ....... G01L 5/164; G01L 5/169; G01L 5/0038; G01L 1/127; A61B 34/35; A61B 2090/064; A61B 2090/065
See application file for complete search history.

(56) References Cited

U.S. PATENT DOCUMENTS 2,623,386 A   12/1952  Baker
3,325,761 A    6/1967  McLellan
(Continued)

FOREIGN PATENT DOCUMENTS

CN    103717355 A    4/2014
CN    105682597 A    6/2016
(Continued)

OTHER PUBLICATIONS

International Search Report and Written Opinion for Application No. PCT/US2021/049792, mailed Jan. 25, 2022, 10 pages.
(Continued)

*Primary Examiner* — Paul M. West

(57) ABSTRACT

A variety of applications can include apparatus and/or methods that provide an axial force transducer. Two coils wound coaxially with respect to each other can be used with a magnet to determine a distance traveled based on application of an axial force to an instrument component. The two coils and magnet can be configured in a number of ways with respect to the instrument component. In various embodiments, the difference between an inductance associated with one of the two coils along with its relation to the magnet and an inductance associated with the other one of the two coils along with its relation to the magnet can be used to determine the axial force on the component of the instrument associated with the distance travelled. Additional apparatus, systems, and methods are disclosed.

20 Claims, 14 Drawing Sheets

(51) Int. Cl.
*A61B 90/00* (2016.01)
*G01L 1/12* (2006.01)
*G01L 5/00* (2006.01)
*G01L 5/169* (2020.01)

(52) U.S. Cl.
CPC ........ *G01L 5/169* (2020.01); *A61B 2090/064* (2016.02); *A61B 2090/065* (2016.02)

(56) References Cited

U.S. PATENT DOCUMENTS

| | | |
|---|---|---|
| 3,358,511 A | 12/1967 | Bargen |
| 4,064,758 A | 12/1977 | Harrison |
| 4,146,864 A | 3/1979 | Bethe |
| 4,507,170 A | 3/1985 | Myhre |
| 5,024,107 A | 6/1991 | Bethe |
| 5,333,504 A | 8/1994 | Lutz et al. |
| 5,625,576 A | 4/1997 | Massie et al. |
| 5,784,542 A | 7/1998 | Ohm et al. |
| 5,855,583 A | 1/1999 | Wang et al. |
| 6,005,199 A | 12/1999 | Harada et al. |
| 6,197,017 B1 | 3/2001 | Brock et al. |
| 6,331,181 B1 | 12/2001 | Tierney et al. |
| 6,394,998 B1 | 5/2002 | Wallace et al. |
| 6,459,926 B1 | 10/2002 | Nowlin et al. |
| 6,494,882 B1 | 12/2002 | Lebouitz et al. |
| 6,594,552 B1 | 7/2003 | Nowlin et al. |
| 6,663,641 B1 | 12/2003 | Kovac et al. |
| 6,817,974 B2 | 11/2004 | Cooper et al. |
| 6,994,708 B2 | 2/2006 | Manzo |
| 7,083,571 B2 | 8/2006 | Wang et al. |
| 7,169,141 B2 | 1/2007 | Brock et al. |
| 7,935,130 B2 | 5/2011 | Williams |
| 8,256,306 B1 | 9/2012 | Bauer et al. |
| 8,306,656 B1 | 11/2012 | Schaible et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,597,280 B2 | 12/2013 | Cooper et al. |
| 8,602,288 B2 | 12/2013 | Shelton, IV et al. |
| 8,620,473 B2 | 12/2013 | Diolaiti et al. |
| 8,628,518 B2 | 1/2014 | Blumenkranz et al. |
| 8,771,270 B2 | 7/2014 | Burbank |
| 8,800,838 B2 | 8/2014 | Shelton, IV |
| 8,945,095 B2 | 2/2015 | Blumenkranz et al. |
| 8,992,565 B2 | 3/2015 | Brisson et al. |
| 9,028,494 B2 | 5/2015 | Shelton, IV et al. |
| 9,192,448 B2 | 11/2015 | Blumenkranz |
| 9,204,923 B2 | 12/2015 | Manzo et al. |
| 9,232,979 B2 | 1/2016 | Parihar et al. |
| 9,671,860 B2 | 6/2017 | Ogawa et al. |
| 9,707,684 B2 | 7/2017 | Ruiz et al. |
| 9,782,214 B2 | 10/2017 | Houser et al. |
| 9,952,107 B2 | 4/2018 | Blumenkranz et al. |
| 10,085,809 B2 | 10/2018 | Blumenkranz et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,238,458 B2 | 3/2019 | Verner et al. |
| 10,398,433 B2 | 9/2019 | Boudreaux et al. |
| 10,595,836 B2 | 3/2020 | Smaby et al. |
| 10,595,887 B2 | 3/2020 | Shelton, IV et al. |
| 10,653,435 B2 | 5/2020 | Shelton, IV et al. |
| 10,682,141 B2 | 6/2020 | Moore et al. |
| 2003/0135203 A1 | 7/2003 | Wang et al. |
| 2005/0096502 A1 | 5/2005 | Khalili |
| 2005/0119527 A1 | 6/2005 | Banik et al. |
| 2007/0043338 A1 | 2/2007 | Moll et al. |
| 2007/0078484 A1 | 4/2007 | Talarico et al. |
| 2007/0119274 A1 | 5/2007 | Devengenzo et al. |
| 2007/0156019 A1 | 7/2007 | Larkin et al. |
| 2008/0046122 A1 | 2/2008 | Manzo et al. |
| 2008/0065105 A1 | 3/2008 | Larkin et al. |
| 2008/0132893 A1 | 6/2008 | D'Amelio et al. |
| 2008/0221391 A1 | 9/2008 | Weitzner et al. |
| 2009/0088774 A1 | 4/2009 | Swarup et al. |
| 2009/0324161 A1 | 12/2009 | Prisco |
| 2010/0063478 A1 | 3/2010 | Selkee |
| 2010/0219388 A1 | 9/2010 | Schena |
| 2010/0313679 A1 | 12/2010 | Larkin et al. |
| 2011/0071543 A1 | 3/2011 | Prisco et al. |
| 2011/0277775 A1 | 11/2011 | Holop et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0123441 A1 | 5/2012 | Au et al. |
| 2013/0291654 A1 | 11/2013 | Blumenkranz et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0238174 A1 | 8/2014 | Ikebe |
| 2014/0257333 A1 | 9/2014 | Blumenkranz |
| 2014/0330432 A1 | 11/2014 | Simaan et al. |
| 2015/0051034 A1 | 2/2015 | Cooper et al. |
| 2015/0150635 A1 | 6/2015 | Kilroy et al. |
| 2015/0374447 A1 | 12/2015 | Blumenkranz et al. |
| 2017/0007345 A1 | 1/2017 | Smith et al. |
| 2017/0165017 A1 | 6/2017 | Chaplin et al. |
| 2017/0172509 A1* | 6/2017 | Hein .................... A61B 5/6885 |
| 2017/0172687 A1 | 6/2017 | Smith et al. |
| 2017/0215944 A1 | 8/2017 | Keffeler |
| 2018/0042689 A1 | 2/2018 | Mozdzierz et al. |
| 2018/0068773 A1 | 3/2018 | Zhu et al. |
| 2018/0078249 A1 | 3/2018 | Stoy et al. |
| 2018/0206904 A1 | 7/2018 | Felder et al. |
| 2019/0069966 A1 | 3/2019 | Petersen et al. |
| 2019/0094084 A1 | 3/2019 | Swinehart et al. |
| 2019/0125354 A1 | 5/2019 | Deck et al. |
| 2019/0175188 A1 | 6/2019 | PV R |
| 2019/0175887 A1 | 6/2019 | Shameli |
| 2019/0201018 A1 | 7/2019 | Shelton, IV et al. |
| 2019/0223960 A1 | 7/2019 | Chaplin et al. |
| 2019/0223966 A1 | 7/2019 | Holop et al. |
| 2019/0239965 A1 | 8/2019 | Abbott |
| 2019/0249759 A1 | 8/2019 | Abbott |
| 2019/0336228 A1 | 11/2019 | Blumenkranz et al. |
| 2020/0015876 A1 | 1/2020 | Chou et al. |
| 2020/0173525 A1 | 6/2020 | Cooper et al. |
| 2020/0208711 A1 | 7/2020 | Pu et al. |
| 2020/0278265 A1 | 9/2020 | Suresh |
| 2020/0405375 A1 | 12/2020 | Shelton, IV et al. |
| 2021/0033478 A1 | 2/2021 | Shang |
| 2021/0045819 A1 | 2/2021 | Castillo et al. |
| 2021/0045825 A1 | 2/2021 | Lee et al. |
| 2021/0353352 A1 | 11/2021 | Petersen |
| 2021/0401524 A1 | 12/2021 | Suresh et al. |
| 2022/0003615 A1 | 1/2022 | Kadokura |
| 2023/0363849 A1 | 11/2023 | Comenencia et al. |
| 2024/0090959 A1 | 3/2024 | Deyanov |
| 2024/0148405 A1 | 5/2024 | Moreira, I et al. |

FOREIGN PATENT DOCUMENTS

| | | |
|---|---|---|
| CN | 109630582 A | 4/2019 |
| DE | 1147411 B | 4/1963 |
| EP | 0590713 A2 | 4/1994 |
| EP | 2362285 A2 | 8/2011 |
| EP | 2431000 A2 | 3/2012 |
| JP | 2000172355 A * | 6/2000 |
| KR | 100778387 B1 | 11/2007 |
| WO | WO-2007143859 A1 | 12/2007 |
| WO | WO-2009123891 A1 | 10/2009 |
| WO | WO-2012166806 A1 | 12/2012 |
| WO | WO-2014151952 A1 | 9/2014 |
| WO | WO-2015069887 A1 | 5/2015 |
| WO | WO-2017064303 A1 | 4/2017 |
| WO | WO-2018075527 A1 | 4/2018 |
| WO | WO-2019099562 A1 | 5/2019 |
| WO | WO-2020102774 A1 | 5/2020 |
| WO | WO-2020102776 A1 | 5/2020 |
| WO | WO-2020102778 A1 | 5/2020 |
| WO | WO-2020102780 A1 | 5/2020 |
| WO | WO-2021055276 A1 | 3/2021 |

(56) References Cited

FOREIGN PATENT DOCUMENTS

| WO | WO-2021076765 A1 | 4/2021 |
|----|------------------|--------|
| WO | WO-2021097386 A1 | 5/2021 |
| WO | WO-2021219396 A1 | 11/2021 |
| WO | WO-2022056213 A1 | 3/2022 |
| WO | WO-2022/132885   | 6/2022 |

OTHER PUBLICATIONS

Office Action for Chinese Application No. CN202080066153.X, mailed Nov. 30, 2023, 20 pages.
Hazel D., "Comparing Strain Gage Measurements to Force Calculations in a Simple Cantilever Beam," Worcester Polytechnic Institute Major Qualifying Project, Jan. 27, 2016, 39 pages.
International Search Report and Written Opinion for Application No. PCT/US2020/050696, mailed Feb. 18, 2021, 14 pages.
Invitation to Pay Additional Fees and International Search Authority for PCT/US202020/050696, mailed Nov. 24, 2020, 10 pages.
Mertmann M., et al., "Grippers for the Micro Assembly Containing Shape Memory Actuators and Sensors," Le Journal de Physique IV France 7 (1997), Conference C5, Supplement of Journal de Physique III of Nov. 1997, pp. C5-621-C5-626.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Office Action for Chinese Application No. CN202080066153, mailed Oct. 12, 2024, 15 pages.

\* cited by examiner

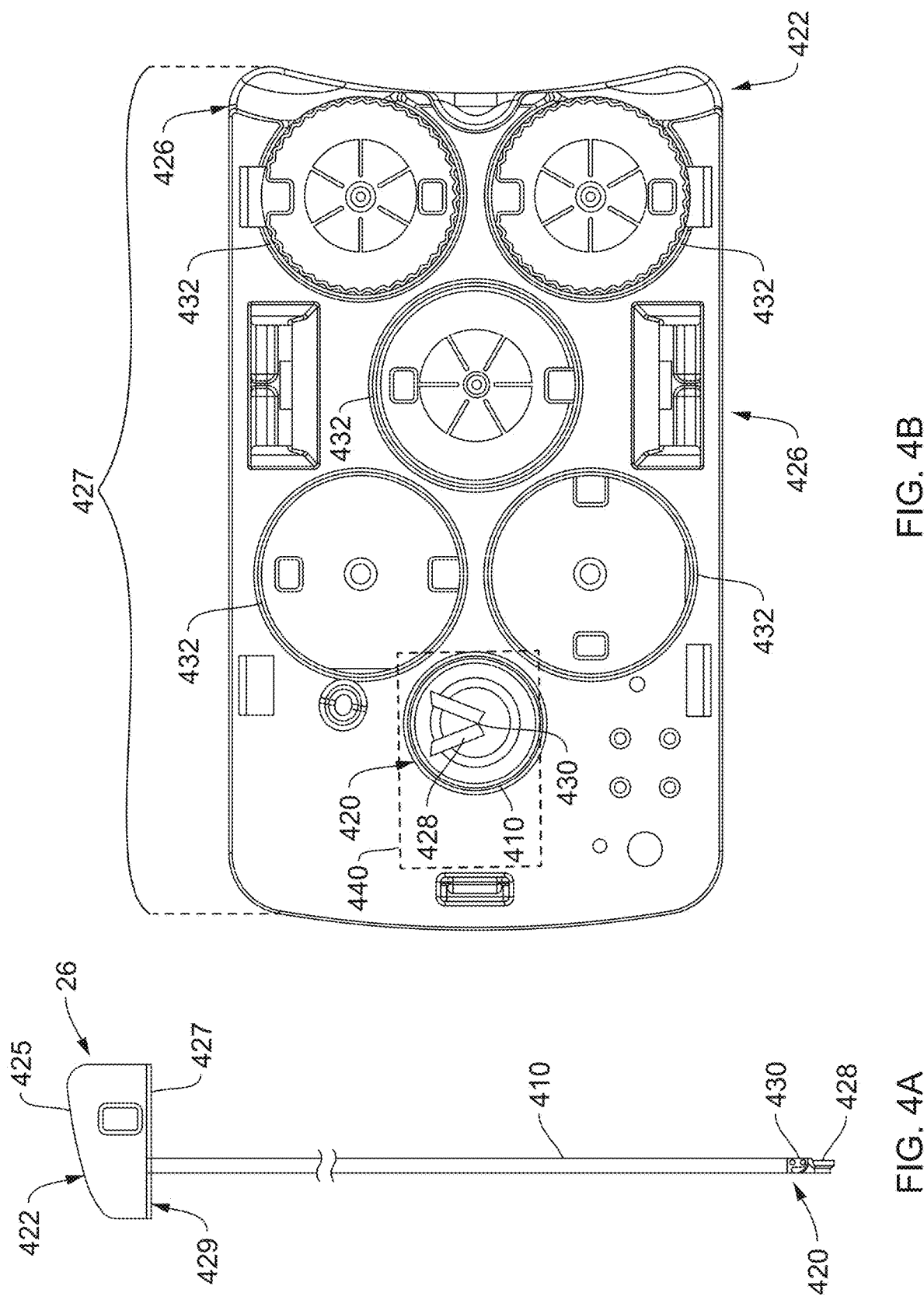

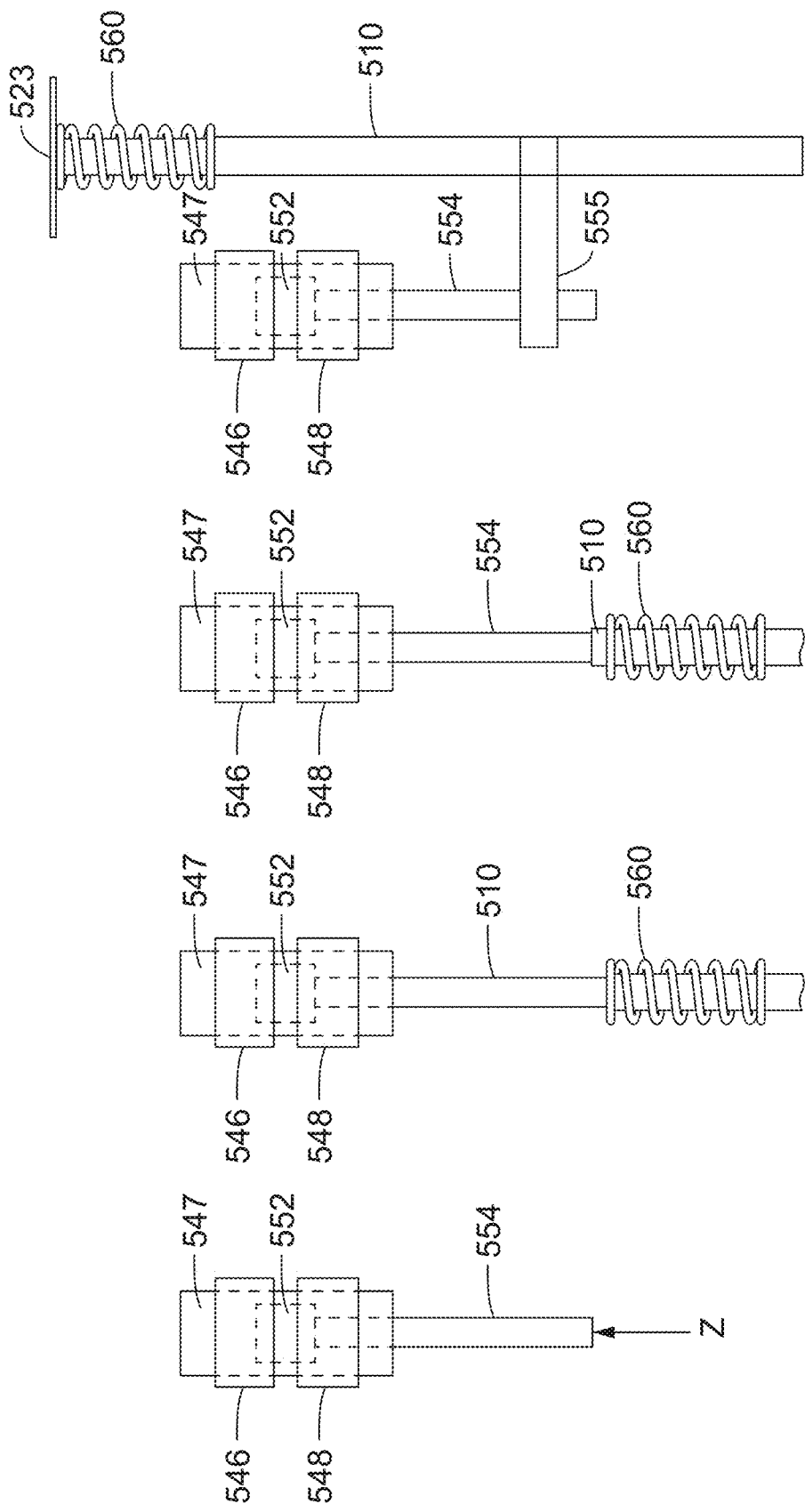

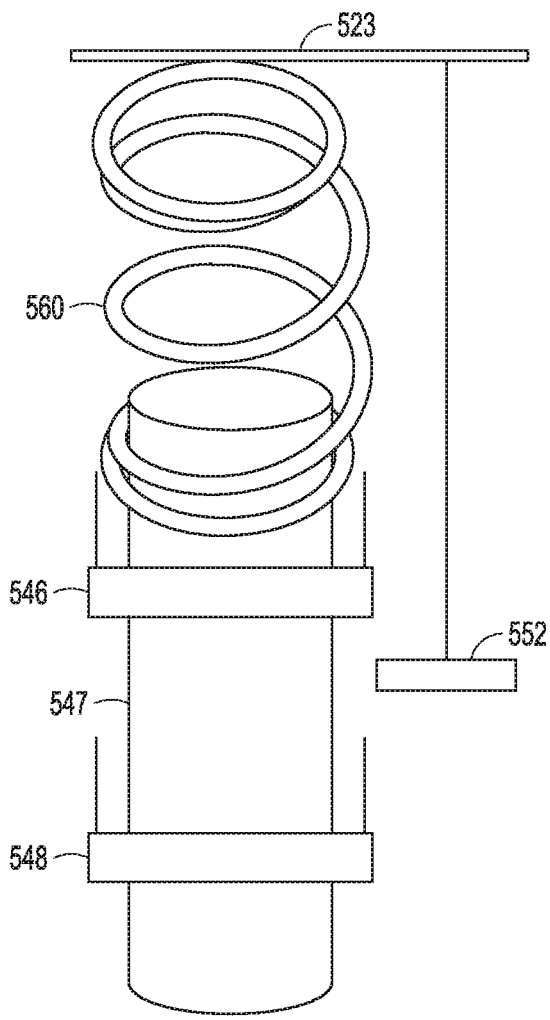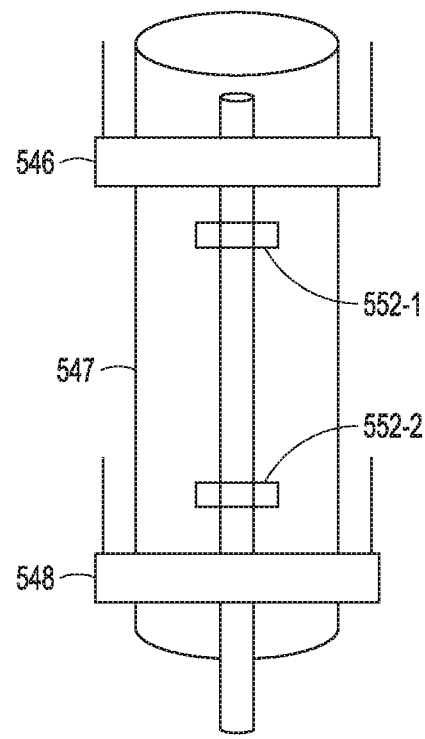
FIG. 5G
FIG. 5H

COMPACT, DIFFERENTIAL, COAXIAL INDUCTIVE FORCE SENSOR

RELATED APPLICATIONS

This patent application is a U.S. national stage filing under 35 U.S.C. § 371 of International Application No. PCT/US2020/050696, entitled "COMPACT, DIFFERENTIAL, COAXIAL INDUCTIVE FORCE SENSOR," filed Sep. 14, 2020, which claims priority to and the filing date benefit of U.S. Provisional Patent Application No. 62/901, 729, entitled "COMPACT, DIFFERENTIAL, COAXIAL INDUCTIVE FORCE SENSOR" filed Sep. 17, 2019, each of the disclosures of which is incorporated by reference herein in its entirety. This application is related to U.S. Provisional Patent Application No. 63/077,833, entitled "Devices and Methods for Compact, Redundant Inductive Force Sensor," and filed on Sep. 14, 2020, the disclosure of which is incorporated herein by reference in its entirety.

BACKGROUND

The embodiments described herein relate to force sensing mechanical structures, more specifically to medical devices, and still more specifically to instruments used for minimally invasive surgery. More particularly, the embodiments described herein relate to medical devices that include a force sensor unit that is coupled to a mechanical structure of the medical device and is used to measure axial forces applied to the end effector of the medical device during a surgical procedure.

Minimally invasive medical techniques are intended to reduce the amount of tissue that is damaged during diagnostic or surgical procedures, thereby reducing patient recovery time, discomfort, and deleterious side effects. Teleoperated surgical systems that use robot assisted technology can be used to overcome limitations of manual laparoscopic and open surgery. Advances in telepresence systems provide surgeons views inside a patient's body, an increased number of degrees of motion of surgical tools, and the ability for surgical collaboration over long distances. In teleoperation surgery systems, a tool operator can actuate an input to a master control device to send control signals to a mechanical control device at a proximal end portion of an elongated tool shaft to control motion of a connector, such as a cable, or a connector-hypotube combination that extends within a length of the shaft, to control movement of an end effector at a distal end portion of the tool shaft. Control connectors or connector-hypotube combinations, typically are pre-tensioned to enable a surgical tool at a surgical site to respond rapidly and accurately to actuation signals. Thus, direct natural force feedback to a tool operator is largely eliminated because such tool user does not manually manipulate the tool directly.

A force sensor can be disposed at or near a tool shaft to measure clinical forces imparted to patient tissue during a medical procedure due to contact with an end effector, for example. These force measurements at or near a tool shaft can be used to produce haptic feedback forces at an input to a master control device to provide to a user an indication of the forces imparted by the tool to patient tissue, for example. Enhancements to force sensor systems can lead to more accurate force measurements, which in turn, can result in more accurate haptic feedback.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, an apparatus includes a mechanical structure and a force sensor unit coupled to the mechanical structure. The force sensor unit comprises a rod, a magnet coupled to the rod, a first coil coupled to the mechanical structure, and a second coil coupled to the mechanical structure and coaxial with the first coil. The rod comprises a distal portion and a proximal portion, and a center axis of the rod is defined between the proximal and distal portions of the rod. The magnet translates within the first coil and the second coil along the center axis of the rod.

In some embodiments, the apparatus further comprises a shaft coupled to the mechanical structure and the shaft is operably coupled to the rod such that translational movement of the shaft relative to the mechanical structure moves the rod along the center axis of the rod. In some embodiments, the shaft comprises a proximal end and a distal end, and a center axis of the shaft is defined between the proximal and distal ends of the shaft. The shaft is coupled to the mechanical structure such that a linear displacement of the shaft along the center axis of the shaft is in proportion to a force imparted to the shaft in a direction along the center axis of the shaft.

In some embodiments, the center axis of the rod is in a direction parallel to the center axis of the shaft. In some embodiments, the shaft comprises a proximal end and a distal end and a center axis of the shaft is defined between the proximal and distal ends of the shaft. A first signal generated by the first coil is associated with a position of the magnet with reference to the first coil, and a second signal generated by the second coil is associated with a position of the magnet with reference to the second coil. Where the first signal from the first coil and the second signal from the second coil are associated with a linear displacement of the shaft along the center axis of the shaft.

In some embodiments, the linear displacement of the shaft is in proportion to a force imparted to the shaft in a direction along the center axis of the shaft. In some embodiments, the shaft comprises a proximal end and a distal end and a center axis of the shaft is defined between the proximal and distal ends of the shaft. In such an embodiment, the apparatus further comprises a spring coupled to the shaft and the spring is configured to be displaced in proportion to a force imparted to the shaft in a direction along the center axis of the shaft.

In some embodiments, a first signal generated by the first coil is associated with a position of the magnet with reference to the first coil, and a second signal generated by the second coil is associated with a position of the magnet with reference to the second coil. The force sensor unit comprises a microprocessor coupled to receive the first and second signals.

In some embodiments, the first signal has a first frequency, the second signal has a second frequency different from the first frequency, and the microprocessor is configured to execute instructions to determine a linear displacement of the shaft along the center axis of the shaft based on the first frequency and the second frequency.

In some embodiments, the apparatus includes a first magnet and a second magnet. The first magnet is positioned to move within the first coil, and the second magnet is positioned to move within the second coil.

In some embodiments, a medical device, comprises an instrument shaft comprising a proximal end and a distal end, a medical end effector coupled to the distal end of the shaft, a mechanical structure coupled to the proximal end of the shaft, and a force sensor unit coupled to the mechanical structure and to the instrument shaft. The force sensor unit comprises a first coil wound about a first coil axis, a second coil wound about a second coil axis coaxial with the first coil axis, and a magnet. An instrument shaft axis is defined between the proximal and distal ends of the instrument shaft, and the magnet is operably coupled to the instrument shaft and moves along the first coil axis as the instrument shaft moves along the instrument shaft axis.

In some embodiments, the magnet moves within the first coil as the instrument shaft moves along the instrument shaft axis. In some embodiments, the magnet moves within the first coil and within the second coil as the instrument shaft moves along the instrument shaft axis. In some embodiments, the force sensor unit comprises a rod and the rod is axially aligned with the first coil axis and couples the magnet to the instrument shaft.

In some embodiments, a first signal generated by the first coil is associated with a position of the magnet with reference to the first coil, and a second signal generated by the second coil is associated with a position of the magnet with reference to the second coil. The force sensor unit comprises a microprocessor coupled to receive the first and second signals.

In some embodiments, the first signal has a first frequency and the second signal has a second frequency. The microprocessor is configured to execute instructions to determine a measure of a force on the instrument shaft along the instrument shaft axis based on the first frequency and the second frequency.

In some embodiments, at a unique position of the magnet with reference to the first coil and to the second coil, a first signal is generated by the first coil and a second signal is generated by the second coil, and the first signal from the first coil and the second signal from the second coil are associated with a unique linear displacement of the instrument shaft along the instrument shaft axis.

In some embodiments, the medical device further comprises a spring coupled to the shaft and to the mechanical structure, and the spring is configured to be displaced in proportion to a force imparted to the instrument shaft in a direction along the instrument shaft axis.

In some embodiments, a medical device comprises an instrument support structure, an instrument shaft, and a force sensor unit. The instrument shaft comprises a proximal end and a distal end, and an instrument shaft axis is defined between the proximal and distal ends of the instrument shaft. The force sensor unit comprises a first coil wound about a first coil axis, a second coil wound about a second coil axis coaxial with the first coil axis, and a magnet at least partially within one of the first coil and the second coil. The first coil, the second coil, and the magnet are positioned such that translation of the instrument shaft along the instrument shaft axis with reference to the instrument support structure causes relative movement between the magnet and the first coil along the first coil axis and relative movement between the magnet and the second coil along the second coil axis. In some embodiments, the first coil and the second coil are fixed with reference to the instrument support structure.

In some embodiments, the medical device comprises a proximal mechanical structure, a distal end mechanism, and a connecting member. The distal end mechanism is coupled to the distal end of the instrument shaft and comprises a movable component. The proximal mechanical structure comprises the instrument support structure and an actuator input piece mounted to move with reference to the instrument support structure. The connecting member is coupled between the actuator input piece and the movable component of the distal end mechanism and transmits a tensile force, a compressive force, or both tensile and compressive forces from the actuator input piece to the movable component of the distal end mechanism.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features can be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4A is an illustrative side view of a medical device including a distal portion and a proximal mechanical structure coupled to one another by an elongated shaft defining an internal bore, in accordance with various embodiments.

FIG. 4B is an illustrative bottom view of the medical device of FIG. 4A showing the control surface of input device, in accordance with various embodiments.

FIGS. 5A-5H illustrate components of an example force sensor unit, in accordance with various embodiments.

DETAILED DESCRIPTION

The following detailed description refers to the accompanying drawings that show, by way of illustration, various embodiments of the invention. These embodiments are described in sufficient detail to enable those of ordinary skill in the art to practice these and other embodiments. Other embodiments may be utilized, and structural, logical, mechanical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

The embodiments described herein can advantageously be used in a wide variety of force sensor applications, such as for grasping, cutting, and manipulating operations associated with minimally invasive surgery. The embodiments described herein can also be used in a variety of non-medical applications such as, for example, teleoperated systems for search and rescue, remotely controlled submersible devices, aerial devices, and automobiles, etc. The embodiments described herein further can be used to determine the forces exerted on (or by) a distal end portion of the instrument during use.

The medical instruments described herein include a force sensor unit that includes a compact differential inductive force sensor to measure forces applied to the end effector of the medical instrument axially in the z-axis direction. As described herein, two inductive coils are wound coaxially around a cylinder and a magnet (e.g., a ferrite bead, EMI (electromagnetic interference) suppression bead, Nickel-zinc bead, etc.; the term "magnet" is described in more detail below) held by a rod is movably positioned within the coils. As the magnet is moved axially within the coils, a change in inductance at each coil results. The change in inductance at each of the coils can be used to measure changes in position of the instrument shaft, which can be translated to z-axis force measurements.

Figure 1:
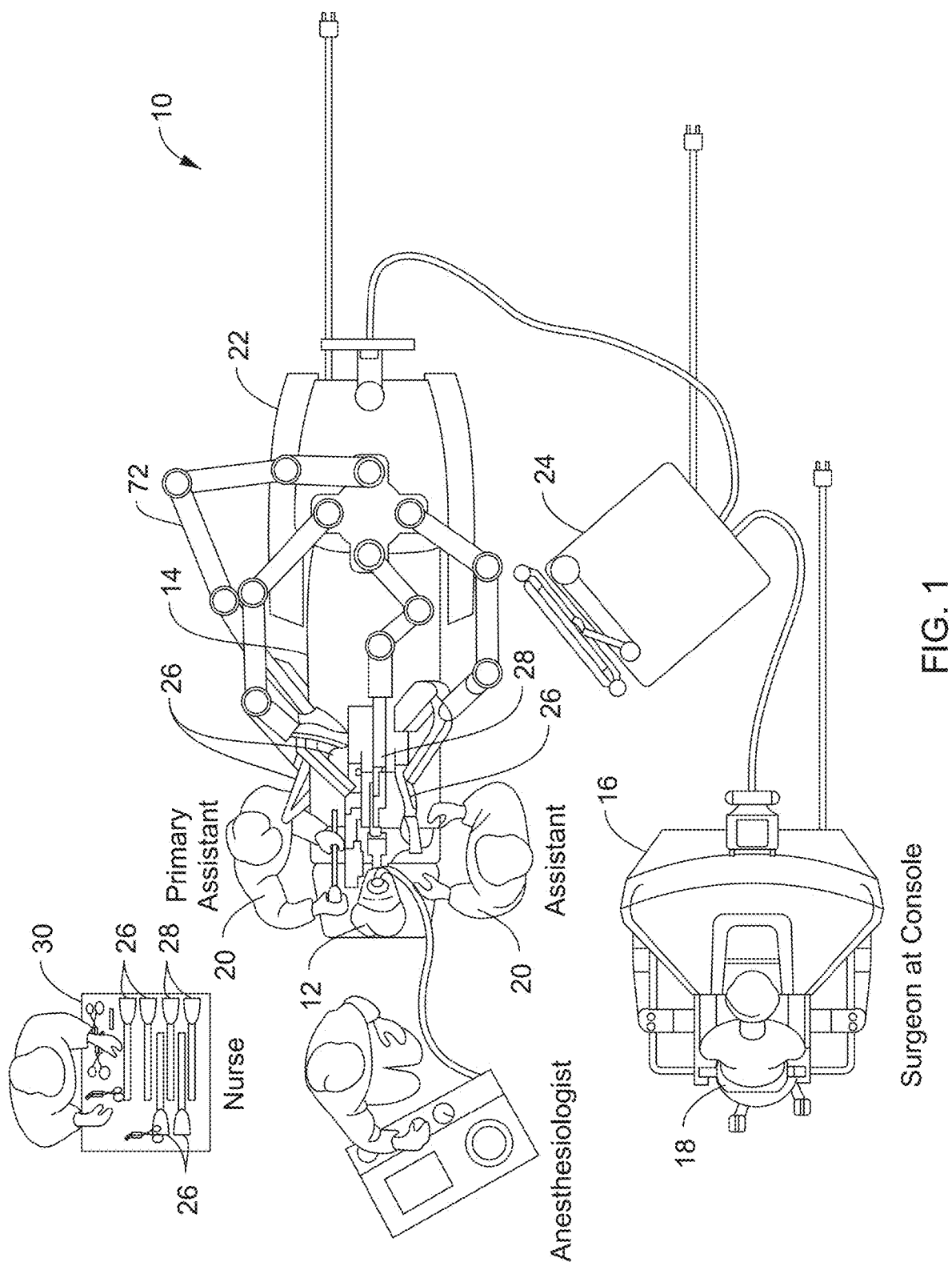
FIG. 1 is an illustrative plan view of a minimally invasive teleoperated surgical system for performing a minimally invasive diagnostic or surgical procedure on a patient who is lying on an operating table, in accordance with various embodiments.

FIG. 1 is an embodiment of an example illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 also can participate in the procedure. The minimally invasive teleoperated surgical system 10 further includes one or more patient-side carts 22 and an electronics cart 24. The patient-side cart 22 can manipulate at least one medical device 26, such as a surgical instrument, through a minimally invasive incision in the body of the patient 12, while the surgeon 18 views the surgical site through the surgeon's console 16. An image of the surgical site can be obtained by an endoscope 28, such as a stereoscopic endoscope, which can be positioned using a mechanical support arm 72 associated with the patient-side cart 22 to orient the endoscope 28 to capture images of the surgical site.

Computer processors located on the electronics cart 24 can be used to process the images of the surgical site for subsequent display to the surgeon 18 through the surgeon's console 16. Moreover, the computer processors at the electronics cart 24 can be configured to process electronic or optical signals indicative of forces imparted at the medical device. The computer processor can produce haptic feedback at the surgeon's console 16, for example. In various embodiments, stereoscopic images can be captured, which allow the perception of depth during a surgical procedure. The number of medical devices 26 used at one time will generally depend on the diagnostic or surgical procedure and the space constraints within the operative site among other factors. If it is necessary to change one or more of the medical devices 26 being used during a procedure, an assistant 20 can remove the medical device 26 from a mechanical support arm 72 associated with patient-side cart 22 and replace it with another medical device 26 from a tray 30 in the operating room.

Figure 2:
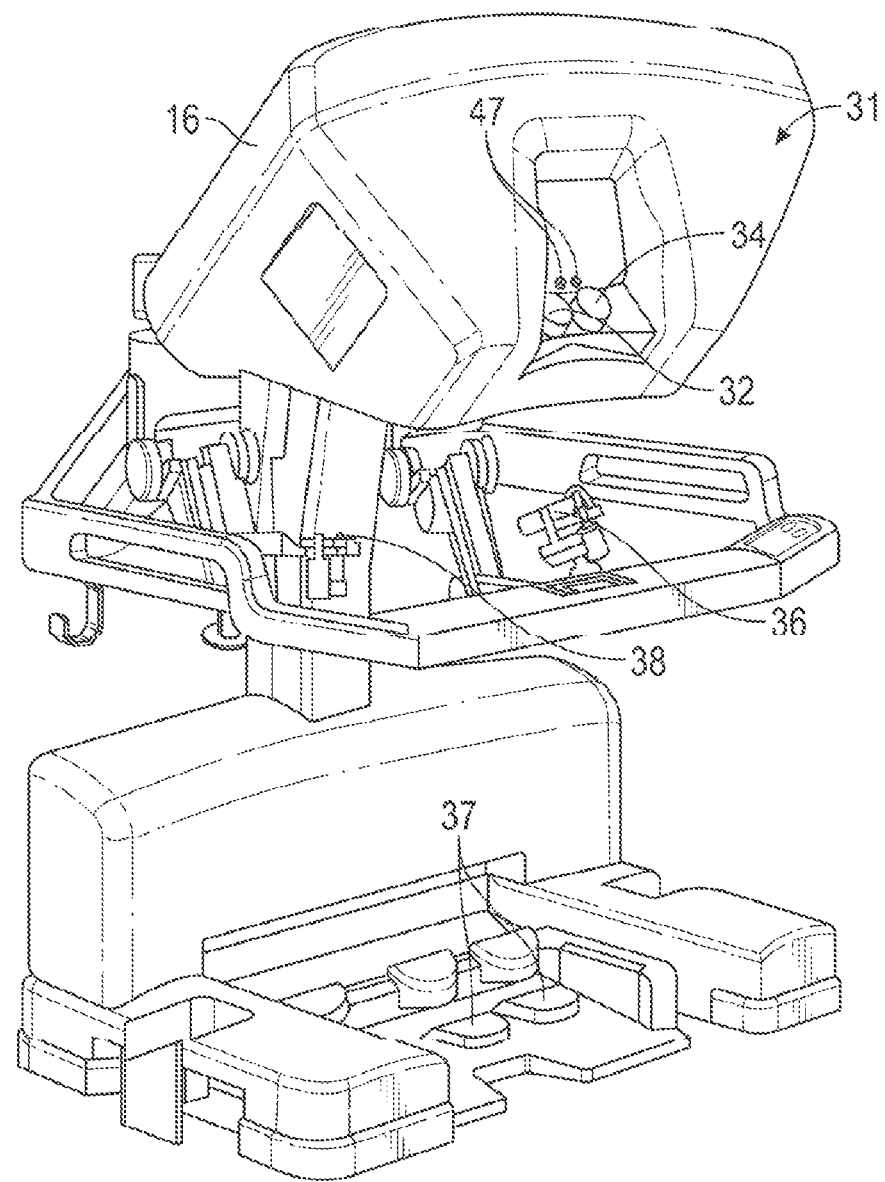
FIG. 2 is a perspective view of a surgeon's console, in accordance with various embodiments.

FIG. 2 is a perspective view of an embodiment of an example surgeon's console 16. The surgeon's console 16 can include a viewer display 31 that includes a left eye display 32 and a right eye display 34 for presenting the surgeon 18 with a coordinated stereoscopic view of the surgical site that enables depth perception. The console 16 can also include one or more hand-operated master control inputs 36, 38 to receive the larger-scale hand control movements. One or more slave medical devices 26 installed for use at on one or more corresponding mechanical support arms 72 of the patient-side cart 22 can move in smaller-scale distances that match a surgeon 18's larger-scale manipulation of the one or more master control inputs 36, 38. The master control inputs 36, 38 can provide the same mechanical degrees of freedom as their associated medical devices 26 to provide the surgeon 18 with telepresence, or the perception that the master control inputs 36 are integral with the slave medical devices 26 so that the surgeon has a keen sense of directly controlling the tools 26. To this end, position, force, and/or tactile feedback sensors (not shown) can be employed to determine tool position, and to measure force, and to measure tactile sensation at the tools 26. The determined tool position and force can be used to produce haptic feedback at a surgeon's hands through the control inputs 36, 38. Electrical or optical signals modulated based upon forces detected at force sensors (not shown) at the tool 26 can be processed by the processors at the electronics cart 24 to produce the haptic feedback at the control inputs 36, 38 that can be indicative of magnitude and direction of the detected forces.

Figure 3:
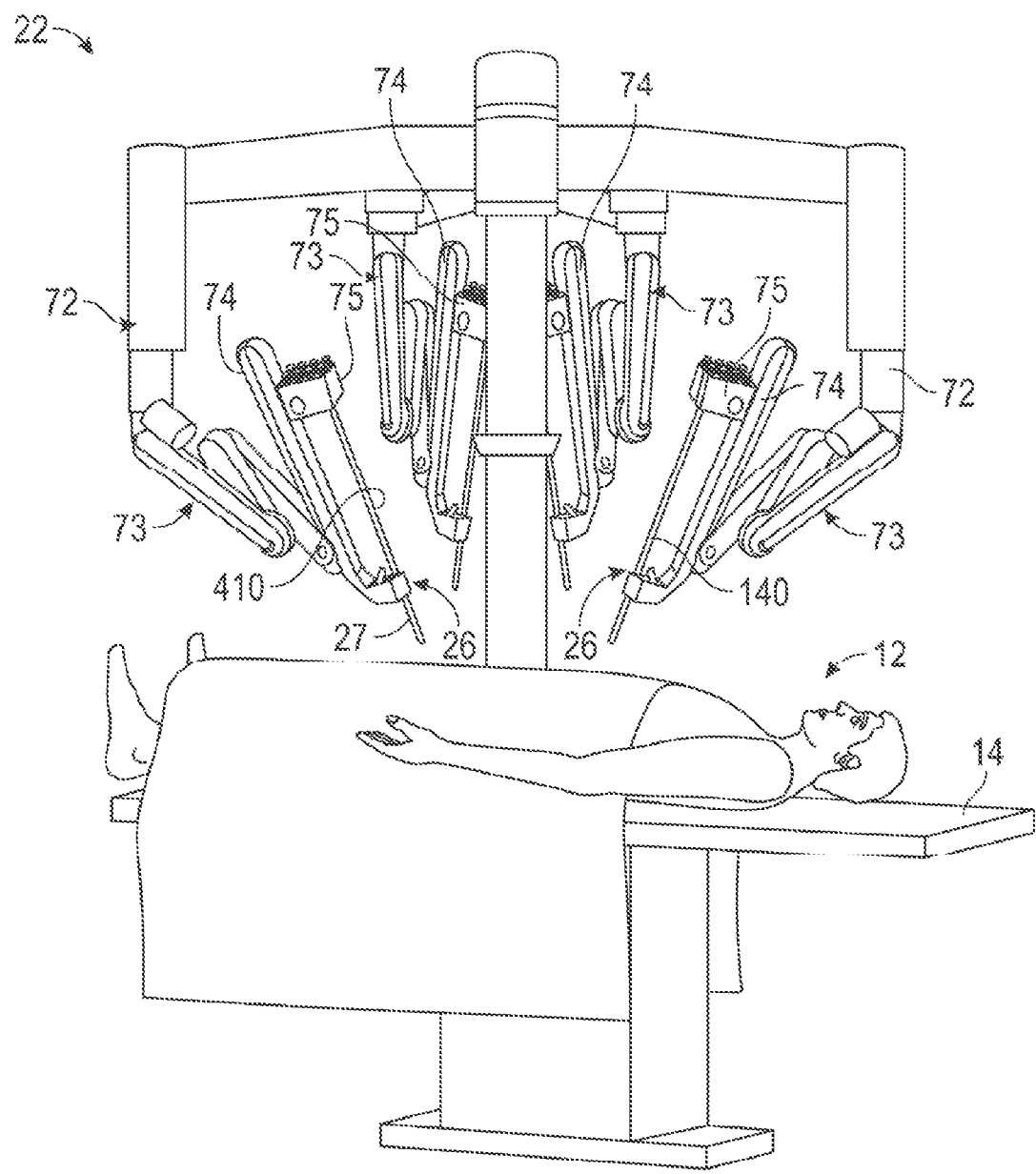
FIG. 3 is a perspective view of a patient-side cart of a minimally invasive teleoperated surgical system, in accordance with various embodiments.

FIG. 3 is a perspective view of an embodiment of an example patient-side cart 22 of a minimally invasive teleoperated surgical system 10. The patient-side cart 22 can include four mechanical support arms 72. Each support arm 72 can include articulated support arm segments 73 that are pivotally mounted end-to-end and a pivotally mounted support forearm 74. A respective medical device carriage 75, which includes motors to control tool motion, is mounted at each support forearm 74. Additionally, each of the support arm 72 can optionally include one or more setup joints (e.g., unpowered and/or lockable) at the junctions of the support arm segments 73 and at the junction with the support forearm 74 that can be used to position the attached medical device carriage 75 in relation to a patient 12 for surgery. Each medical device 26 can be detachably connected to a carriage 75. While the patient-side cart 22 is shown as including four support arms 72, more or fewer support arms 72 can be used. In general, at least one of the medical devices will include a vision system that typically includes an endoscopic camera tool (not shown) for capturing video images and one or more video displays for displaying the captured video images that can be coupled to one of the carriages 75.

Individual medical devices 26 and cannulas 27 can be removably coupled to the carriages 75, with a tool shaft portion 410 of the medical device 26 inserted through the cannula 27. The carriage 75 can house multiple teleoperated actuators such as motors (not shown) that impart motion to drive members, such as drive shafts and capstans (not shown), that in turn, drive connectors coupled to an end effector that the medical device 26 translates into a variety of movements of the end effector on the medical device 26. In various embodiments, the teleoperated actuators in the carriage 75 can impart motion to individual components of the medical device 26 such as end effector wrist movement or jaw movement, for example.

A surgeon manipulates the master control inputs 36, 38 to control a tool end effector. An input provided by a surgeon or other medical person to a control input 36 or 38 (a "master" command) is translated into a corresponding action by the medical device 26 (a "slave" response) through actuation of one or more remote motors. In some embodiments, a flexible wire cable-based force transmission mechanism or the like can be used to transfer the motions of each of the remotely located teleoperated motors to a corresponding tool-interfacing capstan (which functions as an actuator or actuator input piece), located at a carriage 75. In various embodiments, a mechanical adapter interface 76 mechanically couples connector drive members within a tool 26 to motors within a carriage.

The term "medical device" is used herein to describe a medical device for insertion into a patient's body and use in performing surgical or diagnostic procedures. A medical device typically includes an end effector associated with one or more surgical tasks, such as forceps, a needle driver, a shears, a bipolar cauterizer, a tissue stabilizer or retractor, a clip applier, an anastomosis device, an imaging device (e.g., an endoscope or ultrasound probe), and the like. In various embodiments, some medical devices can also provide an articulated support, sometimes referred to as a "wrist," for the end effector, so that the position and orientation of the end effector can be manipulated with one or more mechanical degrees of freedom in relation to the tool's shaft 410. Further, many surgical end effectors can include a functional mechanical degree of freedom, such as jaws that open or close, or a knife that translates along a path.

Surgical instruments appropriate for use in one or more embodiments of the present disclosure can control their end effectors with one or more connectors that can be, for example, rods and/or flexible cables. In some examples, rods, which can be in the form of tubes, can be combined with cables to provide a pull, push, or combined "push/pull" or "pull/pull" control of the end effector, with the connectors providing flexible sections as required. A typical elongated tool shaft 410 for a medical device is small, for example five to eight millimeters in diameter. The diminutive scale of the mechanisms in the surgical instrument creates unique mechanical conditions and issues with the construction of these mechanisms that are unlike those found in similar mechanisms constructed at a larger scale, because forces and strengths of materials do not scale at the same rate as the size of the mechanisms. The connectors must fit within the elongated tool shaft 410 and be able to control the end effector through the wrist joint. The connectors can be manufactured from a variety of metal (e.g., tungsten or stainless steel) or polymer (e.g., high molecular weight polyethylene) materials.

FIG. 4A is an illustrative side view of a medical device 26 including a distal portion 420 and a proximal mechanical structure 422 coupled to one another by an elongated shaft 410 defining an internal bore. As used herein, the term "proximal" indicates a location nearer to the center of a body or the point of attachment and the term "distal" indicates a location more distant from the center of a body or the point of attachment. For example, the term "proximal" indicates a location closer to a manipulator arm and the term "distal" indicates a location more distant from the manipulator arm. Mechanical structure 422 can include a support structure that can include, for example, a housing 425 supporting an input device 429. Input device 429 can include an instrument control surface 427. In other embodiments, various support structures optionally may be used, such as a chassis, a frame, a bed, a unitized surrounding outer body of the mechanical structure, and the like. The input device facilitates controlled adjustment of the instrument's end effector via a connector (which functions as, for example, a tension member to actuate the end effector) extending along an internal bore of the elongated tool shaft 410. In some embodiments, the connector can be a cable, a band or the like.

Control surface 427 provides mechanical connections to other control features of medical device 26. During use, instrument control surface 427 couples to a medical device carriage 75 (see, FIG. 3), which provides motor-driven rotational forces to steering inputs 432 at the control surface 427 to control the medical device 26. Distal portion 420 of medical device 26 can be secured to any of a variety of end effectors, such as the forceps 428 shown, a needle driver, a cautery device, a cutting tool, an imaging device (e.g., an endoscope or ultrasound probe), or a combined device that includes a combination of two or more various tools and imaging devices. Further, in the illustrated embodiment, forceps 428 are coupled to the elongated tool shaft 410 by a wrist joint 430, which allows the orientation of the forceps to be manipulated with reference to the elongated tool shaft 424.

FIG. 4B is an illustrative bottom view of the example medical device of FIG. 4A showing the control surface 427 of input device 429. The control surface 427 can rest atop a carriage 75, which includes actuators such as motors (not shown) controlled by control signals produced in response to user input at the control inputs 36, 38, for example. As shown, control surface 427 includes multiple steering inputs 432, each of which governs a different aspect of movement by wrist joint 430 and forceps 428. Of course, more or less steering inputs 432 can be provided in different implementations. When control surface 427 is coupled to tool carriage 75, each of steering inputs 432 interfaces with an actuator (e.g., servo motor, not shown) within the carriage 75 that drives the steering input. In this example, steering inputs 432 are configured to form a direct mechanical engagement with respective rotary actuators (e.g., servo motors) of tool carriage 75. However, other suitable configurations for power transmission can also be used (e.g., indirect mechanical couplings including speed and/or torque converters, fluid couplings, and/or electrical couplings). Each of steering inputs 432 is part of a limited slip capstan and drive shaft assembly that operates a drive cable controlling movement of an end effector such as forceps 428, for example. In various embodiments, the mechanical structure 422 can be structured as a back-end housing that includes a force sensor unit 440 to detect axial force at a distal end of the elongated shaft 410. The force sensor unit 440 may be disposed in the mechanical structure 422 in a number of arrangements. For example, a portion of the force sensor 440 can be arranged over the elongated shaft 410.

A design of a compact, axial force sensor unit, which has components small enough to fit on a proximal end of an instrument shaft, can be implemented using target material with respect to multiple coils to generate signals that can be compared to determine axial motion of the instrument shaft in response to an axial force applied to the distal end of the instrument shaft. The designs described herein are temperature stable, robust against cautery interference, and survives autoclave cleaning. The force sensor unit is frictionless, not disturbing the force being measured.

In various embodiments, a dual-coil distance displacement sensor can be used in conjunction with a spring or flexure to determine the axial force imparted upon an instrument shaft. Since force is bi-directional, the spring can be structured as a bi-directional spring. The axial direction can be taken as a z-axis direction. A z-direction force upon a distal end of the instrument shaft displaces the instrument shaft axially in the proximal direction of the instrument shaft. With the spring operatively coupled to a proximal end portion of the instrument shaft, the spring is displaced by a distance proportionate to a z-direction force imparted to a distal portion of the instrument shaft. The dual-coil displacement sensor can include a proximal coil and a distal coil, which are coaxially mounted in fixed positions upon a support structure of a proximal mechanical structure to measure axial displacement of the spring based upon change in magnetic flux through the coils or the inductance within the coils, as described in more detail below.

The proximal end of the instrument shaft or a component coupled to the proximal end of the instrument shaft, can include a magnet disposed thereon. Any of the magnets described herein can be, for example, a ferrite bead, an EMI suppression bead, a Nickel-zinc bead, or any other suitable material. Thus, in one aspect it should be understood that the term "magnet" as used herein can refer to any component or material coupled to the instrument shaft that can be used to provide a signal indicative of the position of the shaft within the coils as the magnet moves within the coils. The magnet can be in the form of a bead, though other forms may be used. The magnet can be disposed or connected to the instrument shaft in a number of ways. With the magnet connected to the instrument shaft, movement of the instrument shaft results in movement of the magnet. The proximal end of the instrument shaft (or an extension of the instrument, a rod, or the like) with the magnet thereon extends through the dual windings such that there is an air gap between the instrument shaft (or rod) with the magnet disposed thereon and the dual-coils. When "at rest," with no z-direction force exerted upon the instrument shaft, the instrument shaft can be axially positioned such that the magnet is disposed in part within each coil. In some embodiments, with no z-direction force exerted upon the instrument shaft, equal portions of the magnet can be disposed within each of the coils. Each coil is coupled into a separate LC circuit in which the coil acts as an inductor (L) and in which the inductance varies with the amount of the magnet contained within the coil. The resonant frequency of each circuit varies with changes in inductance of the circuit. Materials other than a magnetic material can be used, where such other materials contribute or influence the inductance associated with the coils used in the LC circuits. For example, these other materials can be used in the configurations discussed with respect to FIGS. 5A-9.

The inductance of each coil, and therefore, the resonant frequency of each circuit varies with z-axis force upon the distal end portion of the instrument shaft. With the spring operatively coupled to the proximal end portion of the instrument shaft, the spring displacement in response to z-direction force upon the distal portion of the instrument shaft corresponds to the amount of axial displacement of the instrument shaft and the axial displacement of the magnet thereon. The amount of axial displacement of the magnet determines the portion of the magnet extending into each coil. For example, a larger z-direction force causes more of the magnet to be disposed within the proximal coil than within the distal coil.

A frequency detection circuit can be used to detect the resonant frequencies of the circuit including the proximal coil and the circuit including the distal coil. Each circuit of the two circuits will have a resonant frequency defined by its coil and the magnet, where the contribution of the magnet is based on a distance of the magnet in the z-direction within the respective coil. When the magnet is disposed within the proximal coil more than within the distal coil, the resonant frequency of the circuit using the proximal coil will be different from the resonant frequency of the circuit using the distal coil. The resonant frequencies can be used to determine the axial displacement of the shaft, and, therefore, the amount of displacement of the spring, from which correspondingly, a measure of the z-direction force upon the distal portion of the shaft can be determined.

Figure 4C:
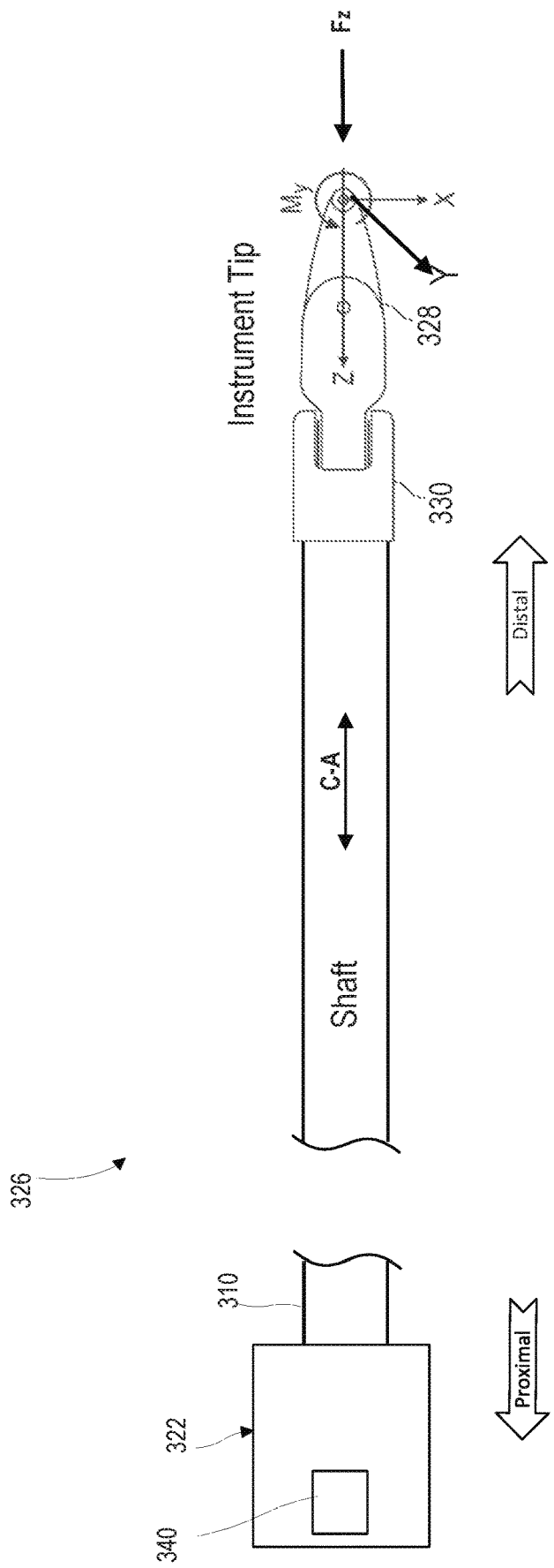
FIG. 4C is a diagrammatic illustration of a medical device including a force sensor unit, according to an embodiment.

FIG. 4C is a schematic illustration of a medical device 326, according to an embodiment. In some embodiments, the medical device 326 or any of the components therein are optionally parts of a surgical system that performs surgical procedures, and which can include a manipulator unit, a series of kinematic linkages, a series of cannulas, or the like as described above with reference to FIGS. 1-4B. The medical device 326 and the medical devices described herein can include a mechanical structure 322 and a force sensor unit 340 coupled to or included within the mechanical structure 322, a shaft 310 coupled to the mechanical structure 322 and an end effector 328 coupled to a distal end of the shaft 310. The end effector 328 can include, for example, articulatable jaws or another suitable surgical tool that is coupled to a link 330. In some embodiments, the link 330 can be included within a wrist assembly having multiple articulating links. In some embodiments, the shaft 310 is also movably coupled at a proximal end portion to the mechanical structure 322. The mechanical structure 322 can include components configured to move one or more components of the medical device, such as, for example, the end effector 328. The mechanical structure 322 can be similar to the mechanical structure 422 described herein.

Generally, during a medical procedure, the end effector 328 contacts anatomical tissue, which may result in X, Y, or Z direction forces being imparted on the end effector 328 and that may result in moment forces such as a moment $M_Y$ about a y-direction axis as shown in FIG. 4C. In some embodiments, one or more strain sensors (not shown), which can be strain gauges, can be included in the medical device 326 to measure strain that can be used to determine forces imparted on the end effector 328 in the X and Y axes directions. These X and Y axes forces are transverse (e.g., perpendicular) to the Z axis (which is parallel or collinear with a center axis of the shaft).

The force sensor unit 340 (and any of the force sensor units described herein) can be used to measure the axial force(s) (i.e., in the direction of the Z-axis parallel to the center axis of the shaft) imparted on the end effector 328. For example, an axial force imparted to the end effector 328 in a direction of the Z-axis can cause axial displacement of the shaft 310 in a direction along a center axis C-A of the shaft 310. The axial force may be in the proximal direction (e.g., a reactive force resulting from pushing against tissue with the end effector) or it may be in the distal direction (e.g., a reactive force resulting from pulling tissue grasped with the end effector). As described herein, the shaft 310 can be coupled to the mechanical structure 322 via a biasing mechanism (e.g., a spring member) such that the amount of travel of the shaft 310 relative to the mechanical structure 322 can be correlated to the magnitude of the axial force imparted to the end effector 328. In this manner, measuring the distance through which the shaft 310 moves relative to the mechanical structure 322 can be used to determine the axial force.

In some embodiments, the force sensor units described herein can include any suitable components to isolate the axial movement of the shaft (i.e., to constrain the shaft such that the measured movement is caused only by the axial force and not the transverse forces along the X and Y axes), and limit frictional force opposing movement of the shaft (which can cause errors in determining the axial force). In some embodiments, the force sensor unit can include a coil assembly and a microprocessor.

As described herein, the coil assembly of the force sensor unit measures the displacement of the shaft along the z-axis, which is then converted to the force measurement. The coil assembly can include two inductive coils each wound around a cylinder formed from a nonconductive material, such as, for example, PEEK. The two coils can be positioned coaxially relative to each other and coupled to, or within, the mechanical structure. In some embodiments, a rod is movable within an interior of the coils and is coupled to the instrument shaft of the medical device. In alternative embodiments, the medical device may not include a rod and instead a proximal portion of the instrument shaft is movable within the coils. The rod can, for example, include a core with a magnet coupled to the core that moves with the rod within the coaxial coils. The core can be, for example, a glass core, a stainless steel core or a core formed with another suitable material. The magnet and any of the magnets described herein, can be, for example, a ferrite bead, an EMI suppression bead, a Nickel-zinc bead, or any other suitable material. Thus, on another aspect it should be understood that the term "magnet" as used herein can refer to any component or material coupled to the core that can be used to provide a signal indicative of the position of the core within the coils as the rod and core move within the coils. The rod is operably coupled to the shaft such that when the shaft moves axially due to forces imparted on a distal end of the medical device, the rod moves with the shaft and within the coils. As the rod moves within the inductive coils, the inductance at each of the coils changes, which can be used to measure changes in position of the instrument shaft. As described above, the change in position of the shaft can be translated to a z-axis force measurement.

During use of the medical device, as force is imparted on the shaft n a z-direction, the shaft will travel along the z-axis, which in turn causes the rod to move along the z-axis. As the rod moves within the coils, each of the coils generate a signal associated with a position of the magnet on the rod within the coils. The microprocessor receives the signals from the coils. For example, in some embodiments, each of the coils generate a signal associated with a linear displacement of the shaft along the center axis of the shaft (e.g., along the z-axis). In some embodiments, the signals from the coils can include a first signal from the first coil having a first frequency, and a second signal from the second coil having a second frequency. The microprocessor is configured to execute instructions to determine from the first frequency and the second frequency a measure of a force on the shaft along the center axis of the shaft. Further details regarding the operation and interaction of the microprocessor are described below with reference to FIG. 7.

Figure 5A:
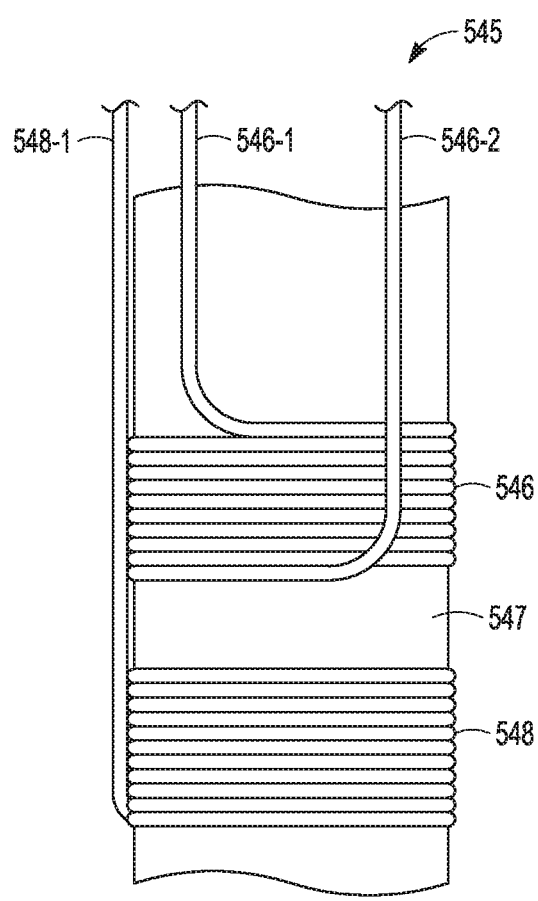
Figure 5B:
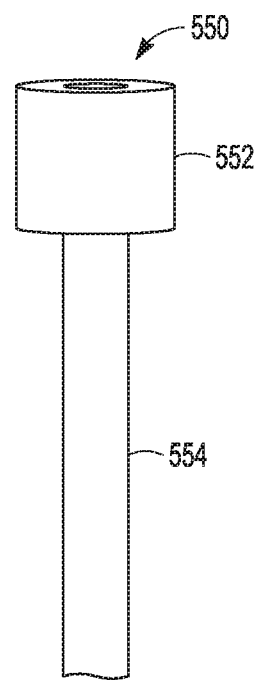

FIGS. 5A-5H illustrate components of an embodiment of an example axial force sensor unit that can be included within a medical device. Since the components in the configurations shown may use some of the same materials, the numbering of the components in FIGS. 5A and 5B are used in the FIGS. 5C-5H. FIG. 5A shows a dual-coil 545 having a first coil 546 displaced from a second coil 548, with the first coil 546 and the second coil 548 affixed to a tube 547. Each of the first coil 546 and the second coil 548 are constructed of electrically conductive material such as with antenna coils. The two electrically conductive coils, the first coil 546 and the second coil 548, can be wound coaxially on the tube 547. The tube 547 can be a plastic tube, such as but not limited to a polyetheretherketone (PEEK) plastic tube for low dimensional change vs. temperature. The first coil 546 and the second coil 548 can be coated with silicone. The use of the silicone coating over the coils allows the coils to remain substantially unaffected (survive) by an autoclave cleaning.

The tube 547 can be coupled to a proximal mechanical structure to which the axial force sensor unit, is coupled to or incorporated within. With the tube 547 coupled to the mechanical structure, the first coil 546 is farther from a distal end of an instrument shaft, to which an applied axial force is to be measured than the second coil 548. Thus, the first coil 546 is a proximal coil and the second coil 548 is a distal coil in the dual-coil arrangement. The proximal coil 546 has leads 546-1 and 546-2 that can be coupled to a capacitor to form a portion of a LC circuit that can be coupled to a precision, dual inductance sensor that measures the inductance of this LC circuit. The distal coil 548 has a lead 548-1 and another lead (not shown) that can be coupled to another capacitor to form a portion of another LC circuit that can be coupled to the precision, dual inductance sensor that can effectively measures the inductance of this other LC circuit.

FIG. 5B shows a configuration 550 having a rod 554 and a magnet 552 on the rod 554 that can be used with the dual-coil 545 of FIG. 5A. The rod 554 rod can also be referred to as a stick. With the magnet 552 being a relatively small structure, the configuration 550 may be referred to as a magnet on a stick or a bead on a stick. The rod 554 has a proximal portion, a distal portion, and a center axis, where the center axis extends between the proximal portion and the distal portion. The rod 554 can be, for example, a glass fiber rod or a stainless steel rod, though other implementations can be used. For example, the rod 554 can include materials such as, but not limited to, quartz, glass, silica, ceramics, and alumina. For example, these other materials for the rod 554 can be used in the configurations discussed with respect to FIGS. 5A-9. The magnet 552 can be disposed on the distal portion of the rod 554. The magnet 552 can be a ferrite structure, which can be implemented as a ferrite bead. The ferrite bead on a stick can be connected to a proximal end of an instrument shaft for which axial force is to be sensed.

FIG. 5C shows an embodiment of an example of a magnet and rod implemented with a dual-coil. The configuration 550 of FIG. 5B can be implemented with the dual-coil of FIG. 5A. The magnet 552 on the rod 554 can be inserted in the tube 547 on which the proximal coil 546 and the axial coil 548 are coaxially wound. The magnet 552 can be a ferrite structure. The two electrically conductive coils, the proximal coil 546 and the distal coil 548, can be wound coaxially on the tube 547. The tube 547 can be a plastic tube, such as but not limited to a polyetheretherketone (PEEK) plastic tube. The proximal coil 546 and the distal coil 548 can be coated with silicone.

The rod 554 is movable in the proximal coil 546 and the distal coil 548; with the magnet 552 disposed upon a proximal portion of the rod 554. The magnet 552 can have a dimension along the center axis of the rod 554 sized for the magnet 552 to be extendable simultaneously within a portion of the proximal coil 546 and within a portion of the distal coil 548. The magnet 552 can be disposed in an initial position centered along the z-axis between the distal coil 546 and the proximal coil 548. This initial position can be a position at which no axial force is applied to an instrument shaft with the rod attached to the instrument shaft. This initial position can provide a zero reference that can be used to determine distance moved by the instrument shaft in response to a force applied to the distal end of the instrument shaft. The initial position can be a position corresponding to a center of the magnet 552 centered between the distal coil 546 and the proximal coil 548 with the magnet 552 within a portion of the proximal coil 546 and extending within a portion of the distal coil 548. In various embodiments, the initial position as a zero reference can be different from the magnet 552 centered between the distal coil 546 and the proximal coil 548. For example, the initial position can depend on the properties of the distal coil 546 and the proximal coil 548 along with the respective capacitors to which the distal coil 546 and the proximal coil 548 are coupled with respect to the measurement arrangement.

The instrument shaft, to which the rod 554 is attached, can be coupled to the mechanical structure through a spring member (not shown in FIGS. 5A-5C). When a force is imparted on a distal end of the instrument shaft in a z-direction (see, e.g., FIG. 5C) along the center axis of the instrument shaft, the spring member is displaced in proportion to that force imparted to the distal end of the instrument shaft. With the distal coil 546 and the proximal coil 548 coupled to a precision, dual inductance sensor, motion of the magnet 552 on the rod 554 within the tube 547 relative to the distal coil 546 and the proximal coil 548 can be detected. This detection can be based on movement of the magnet 552 relative to the initial position.

A dual-coil in an axial force sensor unit can be configured in a number of ways with respect to an instrument shaft to measure an axial force on the instrument shaft. For example, FIG. 5D shows an embodiment of an example of a magnet implemented with a dual-coil with the magnet 552 disposed on a proximal end of an instrument shaft 510 rather than on a rod (e.g., rod 554). The instrument shaft 510 can be coupled to the proximal mechanical structure through a spring member 560 for displacement of the spring member 560 in proportion to a force imparted to the instrument shaft 510 in a direction along the center axis. The use of the dual-coils of FIG. 5D can be similar to the use of the dual-coils of FIG. 5C. The spring member 560 can also be configured in different arrangements than shown in FIGS. 5C-5G.

The proximal end of the instrument shaft 510 can function as the rod 554 of FIG. 5C. The proximal end of the instrument shaft 510 with the magnet 552 thereon can extend in the tube 547 through the dual windings of the proximal coil 546 and the distal coil 548 such that there is an air gap between the instrument shaft 510, with the magnet 552 disposed thereon, and the tube 547 on which the dual-coils are wound. When "at rest," with no axial (z-direction) force exerted upon the instrument shaft 510, the instrument shaft 510 can be axially positioned such that the magnet 552 is disposed partially within each coil. In some embodiments, with no z-direction force exerted upon the instrument shaft 510, equal portions of the magnet 552 can be disposed within each of the coils. Each coil 546 and 548 can be coupled into a separate LC circuit in which the coil acts as an inductor (L) and in which the inductance varies with the amount of the magnetic material contained within the respective coil. The resonant frequency of each circuit varies with changes in inductance of the respective circuit.

FIG. 5E shows an embodiment of an example of a magnet implemented with a dual-coil with the magnet 552 disposed on a proximal end of a rod 554. The rod 554 can be attached to an instrument shaft 510 that can be coupled to a mechanical structure through a spring member 560 for displacement of the spring member 560 in proportion to force imparted to the instrument shaft 510 in a direction along the center axis. The rod 554 can be structured to be attached to the instrument shaft 510 with the rod 554 inserted in the instrument shaft 510. The use of the dual-coils of FIG. 5E can be similar to the use of the dual-coils of FIG. 5C.

The proximal end of the rod 554 with the magnet 552 thereon can extend in the tube 547 through the dual windings of the proximal coil 546 and the distal coil 548 such that there is an air gap between the rod 554 with the magnet 552 disposed thereon, and the tube 547 on which the dual-coils are wound. With movement of the instrument shaft 510, the rod 554 moves axially. When "at rest," with no axial (z-direction) force exerted upon the instrument shaft 510, the rod 554 attached to the instrument shaft 510 can be axially positioned such that the magnet 552 is disposed partially within each coil. In some embodiments, with no z-direction force exerted upon the instrument shaft, equal portions of the magnet 552 can be disposed within each of the coils. Each coil can be coupled into a separate LC circuit in which the coil acts as an inductor (L) and in which the inductance varies with the amount of the magnetic material contained within the respective coil. The resonant frequency of each circuit varies with changes in inductance of the respective circuit.

FIG. 5F shows an embodiment of an example of a magnet 552 implemented with a dual-coil with the magnet 552 disposed on a proximal end of a rod 554. The rod 554 can be attached to an instrument shaft 510, where the instrument shaft 510 can be coupled to a component 523 of a mechanical structure through a spring member 560 for displacement of the spring member 560 in proportion to force imparted to the instrument shaft 510 in a direction along the center axis. The rod 554 can be structured to be attached to the instrument shaft 510 using a support mount 555 to affix the rod 554 to the instrument shaft 510. The center axis of the rod 554 can be aligned in a direction parallel to a center axis of the instrument shaft 510. With the rod 554 attached to the instrument shaft 510 by the support mount 555, as the instrument shaft 510 moves in its axial direction, the rod 554 moves in an axial direction parallel to the center axis of the instrument shaft 510. The use of the dual-coils of FIG. 5F can be similar to the use of the dual-coils of FIG. 5C.

The proximal end of the rod 554 with the magnet 552 thereon can extend in a tube 547 through the dual windings of the proximal coil 546 and the distal coil 548 such that there is an air gap between the rod 554, with the magnet 552 disposed thereon, and the tube 547 on which the dual-coils are wound. When "at rest," with no axial (z-direction) force exerted upon the instrument shaft 510, the rod 554 attached to the instrument shaft 510 can be axially positioned such that the magnet 552 is disposed in part within each coil. In some embodiments, with no z-direction force exerted upon the instrument shaft, equal portions of the magnet 552 can be disposed within each of the coils. Each coil can be coupled into a separate LC circuit in which the coil acts as an inductor (L) and in which the inductance varies with the amount of the magnetic material contained within the respective coil. The resonant frequency of each circuit varies with changes in inductance of the respective circuit.

The dual coils and magnet can be arranged with an instrument shaft in yet other configurations. For example, a proximal coil 546 and a distal coil 548 can be affixed on the moveable instrument shaft 510 with a magnet 552 coupled to a stationary back-end component 523 of a proximal mechanical structure to which the instrument shaft is coupled through a spring 560, as shown in FIG. 5G. In another example, the coils 546 and 548 of a dual-coil configuration can be relatively farther apart on a tube 547 than used in the configurations of FIGS. 5C-5F with two magnets 552-1 and 552-2 on a rod 547 as shown in FIG. 5H, where one of the magnets 552-1 is near the proximal coil 546 and the other magnet 552-2 is near the distal coil 548. Additionally, any of the dual coil/magnet arrangements described herein can be coupled to an instrument shaft and/or within a proximal mechanical structure using any suitable linkage, such as those shown and described in U.S. Provisional Patent Application No. 63/077,833, entitled "Devices and Methods for Compact, Redundant Inductive Force Sensor," incorporated by reference above.

Figure 6B:
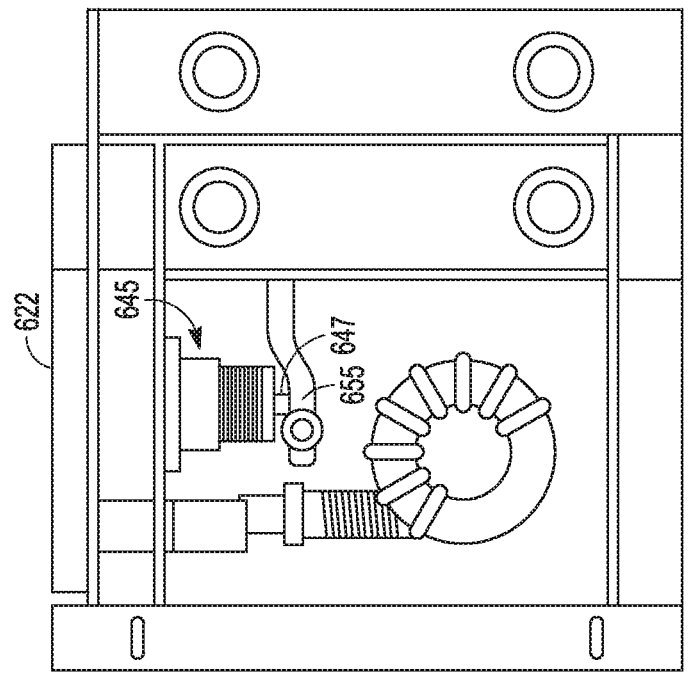
FIG. 6B shows the mechanical structure of FIG. 6A with the dual coils having a rod inserted within the dual coils with the rod affixed to a support mount to couple to the instrument shaft of FIG. 6A, in accordance with various embodiments.
Figure 6A:
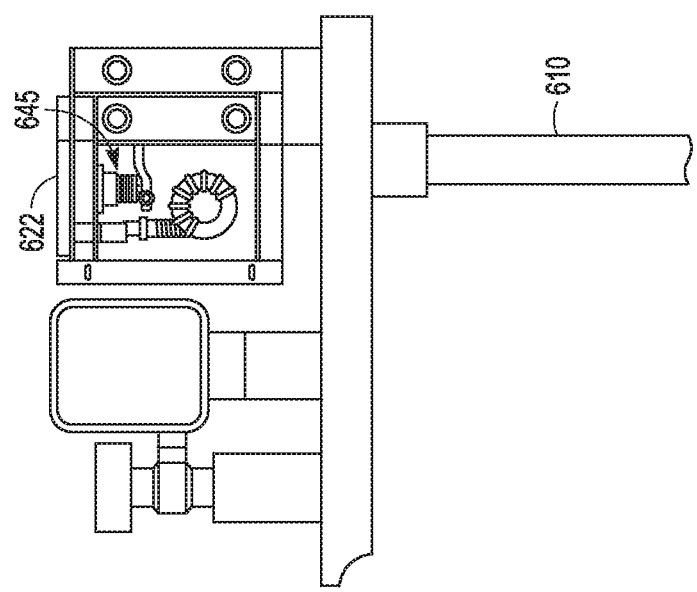
FIG. 6A shows a mechanical structure that can be coupled to an instrument shaft as discussed with respect to FIGS. 5A-5H, in accordance with various embodiments.

FIG. 6A shows a proximal mechanical structure 622 that can be coupled to an instrument shaft 610 as discussed with respect to FIGS. 5A-5H. The mechanical structure 622 includes dual coils 645 to measure an axial force imparted on the distal end of the instrument shaft 610. FIG. 6B shows the mechanical structure 622 of FIG. 6A with the dual coils 645 having a rod 647 inserted within the dual coils 645 with the rod 647 affixed to a support mount 655 to couple to the instrument shaft 610 of FIG. 6A.

Figure 7:
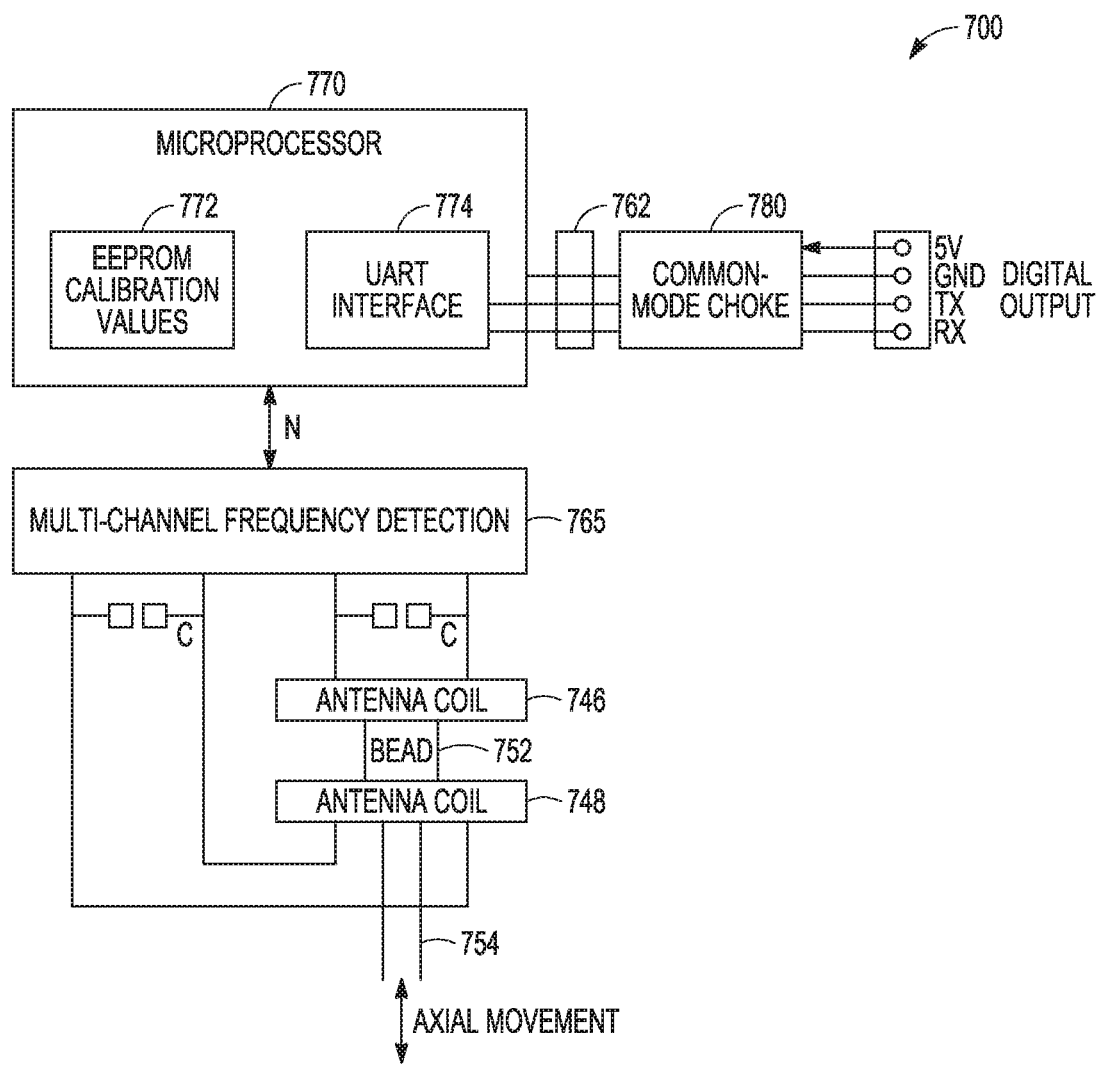
FIG. 7 is a block diagram of an example force sensor that can be implemented to measure axial force applied to an instrument shaft, in accordance with various embodiments.

FIG. 7 is a block diagram of an embodiment of an example force sensor 700 that can be implemented to measure axial force applied to an instrument shaft. The force sensor 700 can be arranged as an inductive z-axis force sensor. An axial force on the instrument shaft results in an axial movement of the instrument shaft, which can be detected by the force sensor 700. The force sensor 700 can include an antenna coil 746 and an antenna coil 748 with a magnet such as a magnetic bead 752 on a rod 754. The antenna coil 746 and the antenna coil 748 can be configured as a proximal coil and a distal coil coaxially positioned relative to each other with a magnet on a rod according to any of the teachings herein associated with one or more of FIGS. 5A-5H and FIG. 6A-6B. In some embodiments, as described herein, a magnet is coupled to the instrument shaft in place of a rod.

The antenna coil 746 can be coupled to a multi-channel frequency detection 765 by a capacitor C that can form a LC circuit with the antenna coil 746 with an inductance contribution based on the distance the magnetic bead 752 moves within the antenna coil 746. The antenna coil 748 can be coupled to the multi-channel frequency detection 765 by a capacitor C that can form a LC circuit with the antenna coil 748 with an inductance contribution based on the distance the magnetic bead 752 moves within the antenna coil 746. The LC circuits associated with the antenna coil 746 and the antenna coil 748 can be implemented with different capacitances, where such differences are taken into account. As the magnetic bead 752 moves closer to the antenna coil 746 than to the antenna coil 748, the inductance contribution to the LC circuit associated with the antenna coil 746 is greater than the inductance contribution to the LC circuit associated with the antenna coil 748. That is, with the magnetic bead 752 centered inside the antenna coils 746 and 748, as the magnetic bead 752 moves axially with the instrument shaft, one coil's inductance increases while the other coil's inductance decreases. The difference of the inductor values indicates the change in force on the shaft. The inductor's temperature change, long term aging, and cautery interference pick-up are the same for both coils. Taking the difference cancels these effects.

The multi-channel frequency detection 765 can be implemented as a precision, dual inductance sensor that measures the inductance. With the capacitor C forming an LC circuit with the antenna coil 746 input to the multi-channel frequency detection 765, the multi-channel frequency detection 765 can output a first signal associated with a frequency of this circuit, for example a ratio of the frequency with a known reference frequency. With the capacitor C forming an LC circuit with the antenna coil 748 input to the multi-channel frequency detection 765, the multi-channel frequency detection 765 can output a second signal associated with a frequency of this circuit, for example a ratio of the frequency with a known reference frequency. The multi-channel frequency detection 765 can output N digital signals to a microprocessor 770. For two LC circuits, the multi-channel frequency detection 765 can output two digital signals to the microprocessor 770.

The microprocessor 770 can include or have access to an EEPROM 772, or other storage device, that can include calibration values for implementation of the magnetic bead 752 with the antenna coil 746 and the antenna coil 748. In determining the axial force on the instrument shaft, the calibration values can be accessed to determine a distance moved based on the frequencies received from the multi-channel frequency detection 765. The difference in frequencies can be stored in the EEPROM 772 as a difference of inductance as a function of distances. This difference of distances can be correlated with a reference position and the difference in inductances. With a distance selected from a measured difference in inductances, the distance can be used with a spring constant stored in the EEPROM 772, where the spring constant is a property of a spring by which the instrument shaft is coupled to a proximal mechanical structure on which the force sensor 700 can be deployed.

The force sensor 700 can include other components. For example, the microprocessor 770 can include a Universal Asynchronous Receiver/Transmitter (UART) interface 774 or other communication interface to transmit (TX) a digital output and receive (RX) a digital signal. The received signal can be used to update calibration values in the EEPROM 772 of the microprocessor 770. A common-mode choke 780 can be used to reduce interference with other boards of the mechanical structure on which the force sensor 700 is deployed. Optionally, the force sensor 700 can include a magnet 762 between the common-mode choke 780 and the microprocessor 770. The magnet 762 can be inserted to help with electromagnetic interference (EMI) radiation reduction. The magnet 762 can be realized as a ferrite bead. Other magnetic material formats can be implemented for the magnet 762.

Figure 8A:
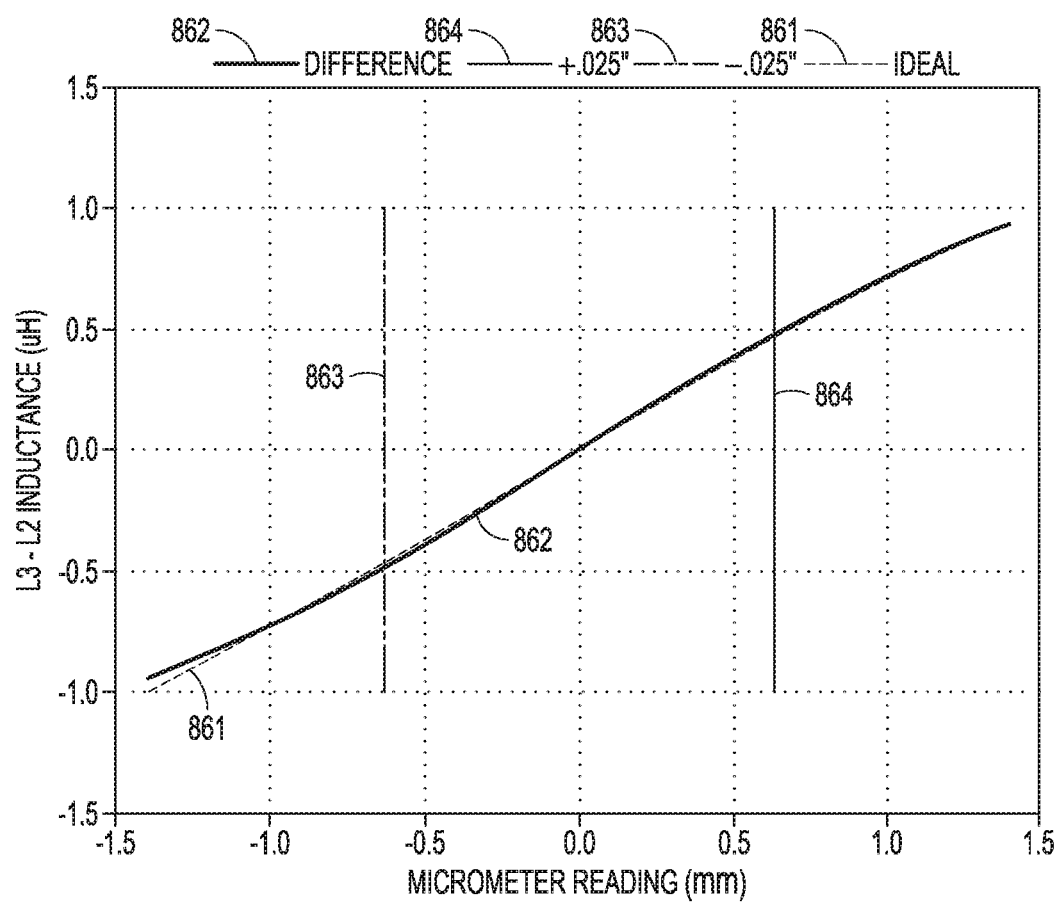
FIGS. 8A-8C shows measurements of inductance versus target position for a magnet target and two coils, in accordance with various embodiments.
Figure 8B:
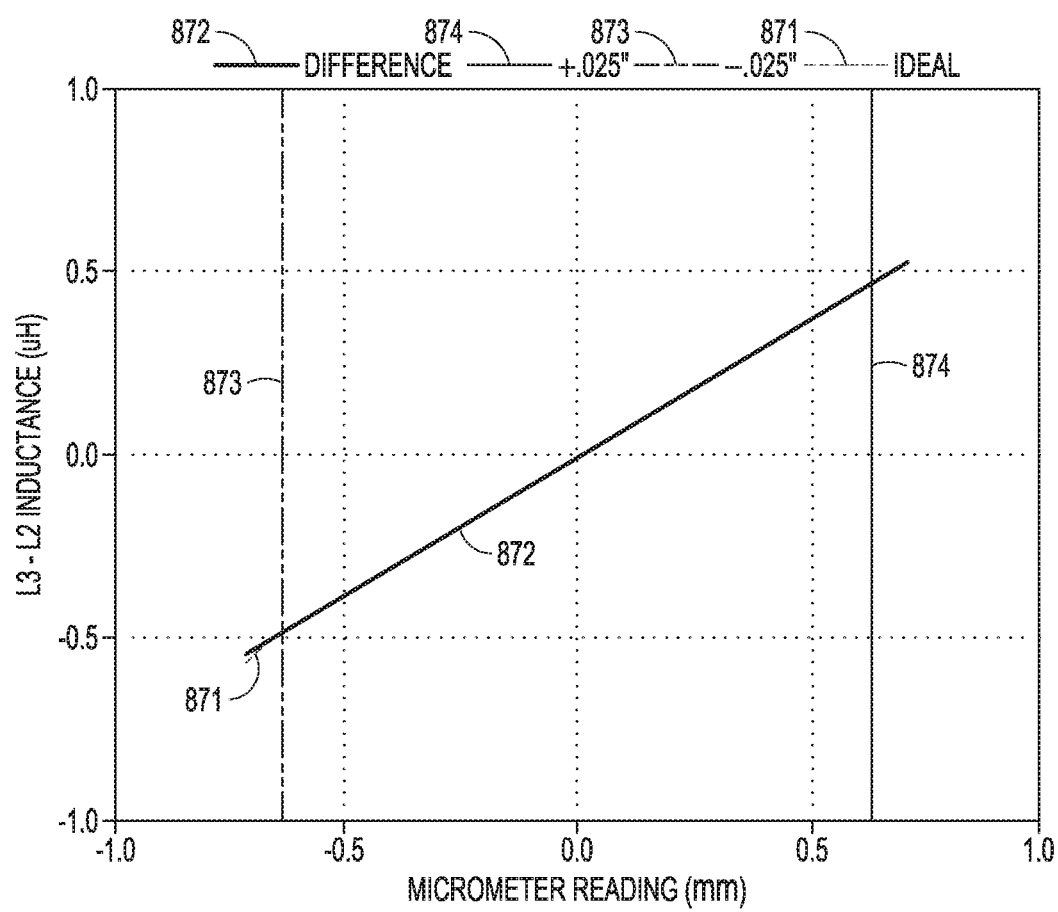
Figure 8C:
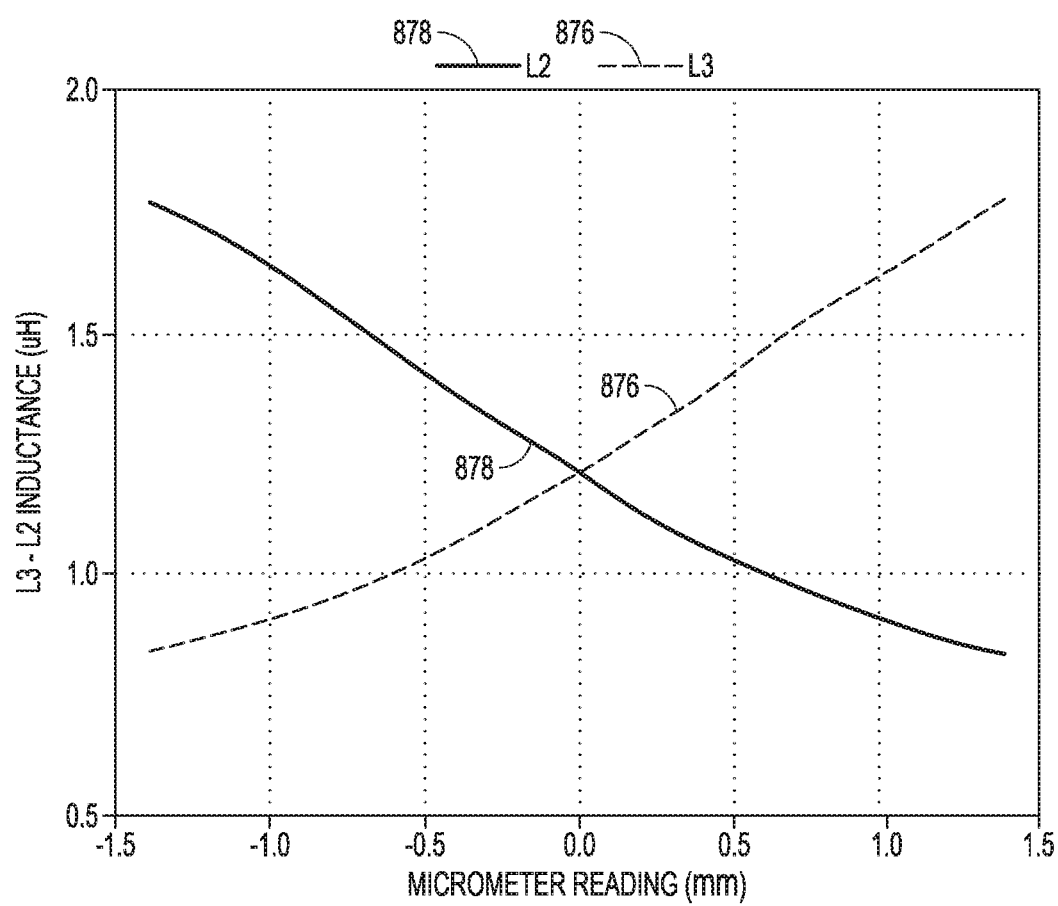

FIGS. 8A-8C show measurements of inductance versus target position for a magnet target and two coils and show values for an axial force on the instrument shaft that causes as a small movement (±0.025 inches) of the shaft relative to the mechanical structure. The target for the shaft displacement (a.k.a. Target Position) was ±0.025 inches. FIG. 8A is a plot of the difference of two inductances labelled L3 and L2 vs. ferrite bead position, which was attached to a micrometer. Curve 862 is the measured difference of two inductances L3 and L2. Curve 861 is the ideal difference of two inductances L3 and L2. The two vertical lines 863 and 864 represent the −0.025 inches and +0.025 inches distances, respectively, from the bead center position.

FIG. 8B shows that the difference L3-L2 is nearly a straight line for inductance difference vs. micrometer (bead) position. Such a measurement can be used to define ranges of operation for the signal from the sensor to linear, since subtraction only works in the linear region. However, the dual coil approach can also work when both coils drift equally and are temperature independent, which can eliminate use of subtraction one from the other. Curve 872 is the measured difference of two inductances L3 and L2. Curve 871 is the ideal difference of two inductances L3 and L2. The two vertical lines 873 and 874 represent the −0.025 inches and +0.025 inches distances, respectively, from the bead center position.

FIG. 8C shows a plot of the inductances L3 and L2 vs. micrometer (bead) position. Curve 876 is the measured inductance L3. Curve 878 is the measured inductance L2.

Figure 9:
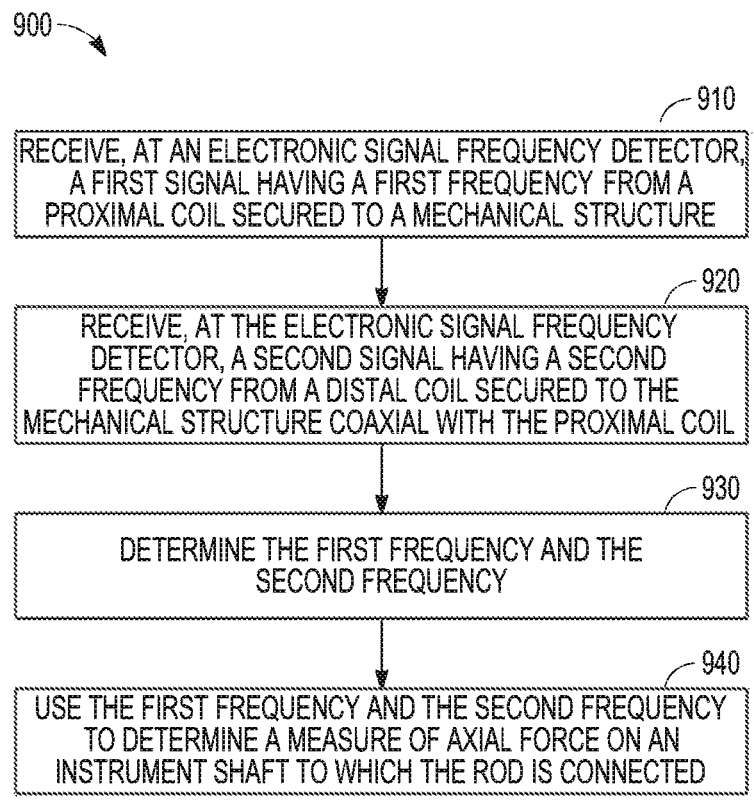
FIG. 9 is a flow diagram of features of an example method of determining axial force, in accordance with various embodiments.

FIG. 9 is a flow diagram of features of an embodiment of an example method 900 of determining axial force. At 910, a first signal having a first frequency from a proximal coil secured to a proximal mechanical structure is received at an electronic signal frequency detector. At 920, a second signal having a second frequency from a distal coil secured to the proximal mechanical structure and coaxial with the proximal coil is received at the electronic signal frequency detector. A rod movable in the proximal coil and the distal coil is used to provide the first and second frequencies with the rod having a magnet disposed upon a proximal portion of the rod. The rod has a proximal portion, a distal portion, and a center axis, with the center axis extending between the proximal portion and the distal portion.

At 930, the first frequency and the second frequency are determined. At 940; the first frequency and the second frequency are used to determine a measure of axial force on an instrument shaft to which the rod is connected. Using the first frequency and the second frequency to determine a measure of axial force on an instrument shaft can include using the first frequency and the second frequency to determine an axial displacement of a spring member through which the instrument shaft is coupled to the proximal mechanical structure.

Variations of the method 900 or methods similar to the method 900 can include a number of different embodiments that may be combined depending on the application of such methods and/or the architecture of systems in which such methods are implemented. Such methods can include converting the first frequency and the second frequency to a first inductance and a second inductance; and generating an identification of a change of force on the instrument shaft using a difference between the first inductance and the second inductance. Such measurements can be used in ranges of operation for the signals from the sensor to linear, since subtraction only works in the linear region. However, the dual coil approach can also work when both coils drift equally and are temperature independent, which can eliminate use of subtraction one from other. The change of force is a measure of axial force on a distal portion of the instrument shaft to which the rod is connected. Since force is bi-directional, the measure of axial force on a distal portion of the instrument shaft is bi-directional.

Variations of the method 900 or methods similar to the method 900 can include converting the first frequency and the second frequency to a first inductance and a second inductance; and generating an identification of a change of force on the instrument shaft using the first inductance and the second inductance for the proximal coil and the distal coil structured as temperature independent coils that drift equally.

A machine-readable storage device may include any non-transitory mechanism for storing information in a form readable by a machine, for example, a computer or a microprocessor tasked to perform specific functions. For example, a machine-readable storage device may include read-only memory (ROM), random-access memory (RAM), magnetic disk storage media, optical storage media, flash-memory devices, and other storage media and media. In various embodiments, a non-transitory machine-readable medium can comprise instructions, which when executed by a set of processors, can cause a system to perform operations comprising: receiving, at an electronic signal frequency detector, a first signal having a first frequency from a proximal coil secured to a mechanical structure; receiving, at the electronic signal frequency detector, a second signal having a second frequency from a distal coil secured to the mechanical structure and coaxial with the proximal coil, with a rod movable in the proximal coil and the distal coil, the rod having a proximal portion, a distal portion, and a center axis, the center axis extending between the proximal portion and the distal portion, the rod having a magnet disposed upon a proximal portion of the rod; determining the first frequency and the second frequency; and using the first frequency and the second frequency to determine a measure of axial force on an instrument shaft to which the rod is connected. In various embodiments, a non-transitory machine-readable medium can comprise instructions, which when executed by a set of processors cause a system to perform operations comprising features of method 900 or similar methods and can include performing functions associated with features associated with FIGS. 1-8C.

In various embodiments, a system can comprise an axial force transducer, where the axial force transducer includes a mechanical structure; a proximal coil secured to the mechanical structure; a distal coil secured to the mechanical structure, the distal coil coaxial with the proximal coil; a rod having a proximal portion, a distal portion, and a center axis, the center axis extending between the proximal portion and the distal portion, the rod movable in the proximal coil and the distal coil; a magnet disposed upon a proximal portion of the rod; and an electronic signal detector to detect a first signal from the proximal coil and a second signal from the distal coil. The electronic signal detector can be implemented as an electronic signal frequency detector to detect a first frequency of the first signal from the proximal coil and a second frequency of the second signal from the distal coil. The axial force transducer may be implemented as the system.

Variations of such a system can include a number of different embodiments that may be combined depending on the implementation for which such systems are designed. Such systems can include the magnet having a dimension along the center axis sized for the magnet to be extendable simultaneously within a portion of the proximal coil and within a portion of the distal coil. Such systems can include the magnet disposed in an initial position centered between the distal coil and the proximal coil.

Such systems can include the rod being attachable to an instrument shaft with the instrument shaft coupled to the mechanical structure through a spring member for displacement in proportion to a force imparted to the instrument shaft in a direction along the center axis. The center axis of the rod can be configured in a direction parallel to a center axis of the instrument shaft. Such systems can include the rod being a glass fiber rod, though other materials for the rod can be used. Such systems can include the axial force transducer of claim 1, wherein the magnet, disposed upon a proximal portion of the rod, being a ferrite structure.

Such systems can include the proximal coil and the distal coil being wound coaxially on a plastic tube, though other materials can be used. The plastic tube can be a polyetheretherketone tube.

Such systems can include the axial force transducer having a microprocessor coupled to receive a first frequency of the first signal and a second frequency of the second signal, with the microprocessor configured to determine, from the first frequency and the second frequency, a measure of axial force on a distal portion of an instrument shaft to which the rod is connected.

In various embodiments, an axial force transducer can comprise: a mechanical structure; a shaft having a proximal portion, a distal portion and a center axis extending between the proximal portion and the distal portion; a spring member operatively coupled to the mechanical structure for displacement in proportion to force imparted to the shaft in a direction along the center axis; a proximal coil secured to the mechanical structure; a distal coil secured to the mechanical structure coaxial with the proximal coil; a magnet disposed upon a proximal portion of the shaft, wherein the magnet has a dimension along the center axis sized for the magnet to be extendable simultaneously within a partial portion of the proximal coil and within a partial portion of the distal coil; wherein the shaft extends within the proximal coil and within the distal coil such that at least a portion of the magnet extends within at least one of the proximal coil and the distal coil; and an electronic signal frequency detector to detect frequency of electrical signals within the at least one of the proximal coil and the distal coil in which the magnet extends.

In various embodiments, an instrument, having an axial force transducer, can comprise: an instrument shaft; a mechanical structure; a spring member to couple the instrument shaft to the mechanical structure for displacement in proportion to force imparted to the instrument shaft in a direction along the center axis; a proximal coil secured to the mechanical structure; a distal coil secured to the mechanical structure coaxial with the proximal coil; a rod having a proximal portion, a distal portion, and a center axis, the center axis extending between the proximal portion and the distal portion, the rod movable in the proximal coil and the distal coil; a magnet disposed upon a proximal portion of the rod; and an electronic signal detector to detect a first signal from the proximal coil and a second signal from the distal coil. The electronic signal detector can be implemented as an electronic signal frequency detector to detect a first frequency of the first signal from the proximal coil and a second frequency of the second signal from the distal coil.

Variations of such an instrument can include a number of different embodiments that may be combined depending on the implementation for which such instruments are designed. Such instruments can include the magnet having a dimension along the center axis sized for the magnet to be extendable simultaneously within a portion of the proximal coil and within a portion of the distal coil.

Such instruments can include the rod being connected to the instrument shaft. The center axis of the rod can be in a direction parallel to a center axis of the instrument shaft.

Such instruments can include a microprocessor coupled to receive a first frequency of the first signal and a second frequency of the second signal, where the microprocessor is configured to determine, using the first frequency and the second frequency, a measure of axial force on a distal portion of the instrument shaft to which the rod is connected. The instrument can include a common-mode choke coupled to the microprocessor to reduce interference with respect to determination of the measure of the axial force. Such instruments can include an additional magnet, with the additional magnet disposed between the common-mode choke and the microprocessor to aid electromagnetic interference radiation reduction. The additional magnet can include a ferrite bead.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. An apparatus, comprising:
a medical instrument comprising a mechanical structure and a force sensor unit coupled to the mechanical structure;
wherein the force sensor unit comprises a rod defining a center axis, a magnet coupled to the rod, a first coil coupled to the mechanical structure at a first axial position along the center axis, and a second coil coupled to the mechanical structure at a second axial position different than the first axial position along the center axis and coaxial with the first coil;
and
wherein the magnet translates within the first coil and the second coil along the center axis of the rod.

2. The apparatus of claim 1, wherein:
the apparatus further comprises a shaft coupled to the mechanical structure; and
the shaft is operably coupled to the rod such that translational movement of the shaft relative to the mechanical structure moves the rod along the center axis of the rod.

3. The apparatus of claim 2, wherein:
the shaft comprises a proximal end and a distal end;
a center axis of the shaft is defined between the proximal and distal ends of the shaft; and
the shaft is coupled to the mechanical structure such that a linear displacement of the shaft along the center axis of the shaft is in proportion to a force imparted to the shaft in a direction along the center axis of the shaft.

4. The apparatus of claim 3, wherein:
the center axis of the rod is in a direction parallel to the center axis of the shaft.

5. The apparatus of claim 2, wherein:
the shaft comprises a proximal end and a distal end;
a center axis of the shaft is defined between the proximal and distal ends of the shaft;
a first signal generated by the first coil is associated with a position of the magnet with reference to the first coil;
a second signal generated by the second coil is associated with a position of the magnet with reference to the second coil; and
the first signal from the first coil and the second signal from the second coil are associated with a linear displacement of the shaft along the center axis of the shaft.

6. The apparatus of claim 5, wherein:
the linear displacement of the shaft is in proportion to a force imparted to the shaft in a direction along the center axis of the shaft.

7. The apparatus of claim 2, wherein:
the shaft comprises a proximal end and a distal end;
a center axis of the shaft is defined between the proximal and distal ends of the shaft;
the apparatus further comprises a spring coupled to the shaft; and the spring is configured to be displaced in proportion to a force imparted to the shaft in a direction along the center axis of the shaft.

8. The apparatus of claim 2, wherein:
a first signal generated by the first coil is associated with a position of the magnet with reference to the first coil;
a second signal generated by the second coil is associated with a position of the magnet with reference to the second coil; and
the force sensor unit comprises a microprocessor coupled to receive the first and second signals.

9. The apparatus of claim 8, wherein:
the first signal has a first frequency;
the second signal has a second frequency different from the first frequency; and
the microprocessor is configured to execute instructions to determine a linear displacement of the shaft along the center axis of the shaft based on the first frequency and the second frequency.

10. The apparatus of claim 1, wherein:
the first coil is a proximal coil;
the second coil is a distal coil;
the magnet is a first magnet and the apparatus comprises and a second magnet;
the first magnet is positioned to move within the first coil; and
the second magnet is positioned to move within the second coil.

11. A medical device, comprising:
an instrument shaft comprising a proximal end and a distal end opposite the proximal end;
a medical end effector coupled to the distal end of the instrument shaft, the end effector configured to contact a patient tissue;
a mechanical structure coupled to the proximal end of the instrument shaft; and
a force sensor unit coupled to the mechanical structure and to a proximal end portion of the instrument shaft;
wherein the force sensor unit comprises a first coil wound about a first coil axis, a second coil wound about a second coil axis coaxial with the first coil axis, and a magnet;
wherein an instrument shaft axis is defined between the proximal and distal ends of the instrument shaft; and
wherein the magnet is operably coupled to the instrument shaft and moves along the first coil axis as the instrument shaft moves along the instrument shaft axis.

12. The medical device of claim 11, wherein:
the magnet moves within the first coil as the instrument shaft moves along the instrument shaft axis.

13. The medical device of claim 11, wherein:
the magnet moves within the first coil and within the second coil as the instrument shaft moves along the instrument shaft axis.

14. The medical device of claim 11, wherein:
the force sensor unit comprises a rod; and
the rod is axially aligned with the first coil axis and couples the magnet to the instrument shaft.

15. The medical device of claim 11, wherein:
a first signal generated by the first coil is associated with a position of the magnet with reference to the first coil;
a second signal generated by the second coil is associated with a position of the magnet with reference to the second coil; and
the force sensor unit comprises a microprocessor coupled to receive the first and second signals.

16. The medical device of claim 15, wherein:
the first signal has a first frequency;
the second signal has a second frequency; and
the microprocessor is configured to execute instructions to determine a measure of a force on the instrument shaft along the instrument shaft axis based on the first frequency and the second frequency.

17. The medical device of claim 11, wherein:
at a unique position of the magnet with reference to the first coil and to the second coil, a first signal is generated by the first coil, and a second signal is generated by the second coil; and
the first signal from the first coil and the second signal from the second coil are associated with a unique linear displacement of the instrument shaft along the instrument shaft axis.

18. The medical device of claim 11, wherein:
the medical device further comprises a spring coupled to the instrument shaft and to the mechanical structure; and
the spring is configured to be displaced in proportion to a force imparted to the instrument shaft in a direction along the instrument shaft axis.

19. A medical device comprising:
an instrument support structure, an instrument shaft, and a force sensor unit;
wherein the instrument shaft comprises a proximal end and a distal end, and an instrument shaft axis is defined between the proximal and distal ends of the instrument shaft;
wherein the force sensor unit comprises a first coil wound about a coil axis at a first axial position, a second coil wound about the coil axis at a second axial position and coaxial with the first coil, the second axial position being spaced apart axially from the first axial position along the coil axis, and a magnet at least partially within at least one of the first coil and the second coil; and
wherein the first coil, the second coil, and the magnet are positioned such that translation of the instrument shaft along the instrument shaft axis with reference to the instrument support structure causes relative movement between the magnet and the first coil along the coil axis and relative movement between the magnet and the second coil along the coil axis.

20. The medical device of claim 19, wherein:
the medical device comprises a proximal mechanical structure, a distal end mechanism, and a connecting member;
the distal end mechanism is coupled to the distal end of the instrument shaft and comprises a movable component;
the proximal mechanical structure comprises the instrument support structure and an actuator input piece mounted to move with reference to the instrument support structure; and
the connecting member is coupled between the actuator input piece and the movable component of the distal end mechanism and transmits a tensile force, a compressive force, or both tensile and compressive forces from the actuator input piece to the movable component of the distal end mechanism.

* * * * *